United States Patent
Minatelli et al.

(10) Patent No.: US 9,974,756 B2
(45) Date of Patent: *May 22, 2018

(54) COMPOSITION AND METHOD TO ALLEVIATE JOINT PAIN USING PHOSPHOLIPIDS AND ASTAXANTHIN

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 85 days.

This patent is subject to a terminal disclaimer.

(21) Appl. No.: 15/271,506

(22) Filed: Sep. 21, 2016

(65) Prior Publication Data

US 2017/0007555 A1    Jan. 12, 2017

Related U.S. Application Data

(60) Division of application No. 14/645,890, filed on Mar. 12, 2015, now Pat. No. 9,913,810, which is a
(Continued)

(51) Int. Cl.
*A01N 31/04*     (2006.01)
*A61K 31/122*    (2006.01)
(Continued)

(52) U.S. Cl.
CPC ............ *A61K 31/122* (2013.01); *A23L 33/10* (2016.08); *A23L 33/115* (2016.08); *A23L 33/12* (2016.08);
(Continued)

(58) Field of Classification Search
None
See application file for complete search history.

(56) References Cited

U.S. PATENT DOCUMENTS

| 4,141,973 A | 2/1979 | Balazs |
| 4,801,539 A | 1/1989 | Akasaka et al. |

(Continued)

FOREIGN PATENT DOCUMENTS

| CN | 102746947 | 10/2012 |
| EP | 0601698 | 6/1994 |

(Continued)

OTHER PUBLICATIONS

Nir et al., "BioAstin Helps Relieve Pain and Improves Performance in Patients With Rheumatoid Arthritis," Health Research and Studies Center, Los Altos, California, Study Report, May 3, 2002, 8 pages.

(Continued)

*Primary Examiner* — Erin M. Bowers
(74) *Attorney, Agent, or Firm* — Allen, Dyer, Doppelt + Gilchrist, P.A.

(57) ABSTRACT

A dietary supplement composition and associated method of use has the composition formulated in a therapeutic amount to treat and alleviate symptoms of joint pain in a person having joint pain. The composition includes astaxanthin and microbial fermented, low molecular weight hyaluronic acid or sodium hyaluronate (hyaluronan). The composition also includes at least one of a phospholipid, glycolipid, and sphingolipid. It is formulated into an oral dosage form and the astaxanthin is 0.1 to 15 percent by weight of the at least one phospholipid, glycolipid, and sphingolipid.

5 Claims, 1 Drawing Sheet

ASTAXANTHIN 3S, 3'S
(3,3'-DIHYDROXY-4,4'-DIKETO-β-CAROTENE)

Related U.S. Application Data continuation-in-part of application No. 14/217,515, filed on Mar. 18, 2014, now Pat. No. 9,238,043, which is a continuation-in-part of application No. 13/914,725, filed on Jun. 11, 2013, now Pat. No. 8,945,608, which is a continuation of application No. 12/840,372, filed on Jul. 21, 2010, now Pat. No. 8,481,072.

(60) Provisional application No. 61/345,652, filed on May 18, 2010, provisional application No. 61/227,872, filed on Jul. 23, 2009.

(51) Int. Cl.

| | |
|---|---|
| A61K 31/728 | (2006.01) |
| A61K 31/661 | (2006.01) |
| A61K 31/6615 | (2006.01) |
| A61K 36/9066 | (2006.01) |
| A61K 45/06 | (2006.01) |
| A61K 31/202 | (2006.01) |
| A61K 31/685 | (2006.01) |
| A61K 31/7028 | (2006.01) |
| A61K 36/05 | (2006.01) |
| A61K 36/185 | (2006.01) |
| A61K 36/324 | (2006.01) |
| A61K 36/74 | (2006.01) |
| A61K 9/48 | (2006.01) |
| A61K 35/60 | (2006.01) |
| A23L 33/10 | (2016.01) |
| A23L 33/115 | (2016.01) |
| A23L 33/12 | (2016.01) |
| A61K 9/00 | (2006.01) |
| A61K 36/02 | (2006.01) |
| A61K 36/535 | (2006.01) |

(52) U.S. Cl.
CPC .............. *A61K 9/0053* (2013.01); *A61K 9/48* (2013.01); *A61K 9/4858* (2013.01); *A61K 31/202* (2013.01); *A61K 31/661* (2013.01); *A61K 31/6615* (2013.01); *A61K 31/685* (2013.01); *A61K 31/7028* (2013.01); *A61K 31/728* (2013.01); *A61K 35/60* (2013.01); *A61K 36/02* (2013.01); *A61K 36/05* (2013.01); *A61K 36/185* (2013.01); *A61K 36/324* (2013.01); *A61K 36/535* (2013.01); *A61K 36/74* (2013.01); *A61K 36/9066* (2013.01); *A61K 45/06* (2013.01); *A23V 2002/00* (2013.01); *A61K 2236/10* (2013.01); *A61K 2236/13* (2013.01); *A61K 2236/33* (2013.01); *A61K 2236/35* (2013.01); *A61K 2236/53* (2013.01)

(56) References Cited

U.S. PATENT DOCUMENTS

| | | | |
|---|---|---|---|
| 5,527,533 | A | 6/1996 | Tso et al. |
| 6,025,327 | A | 2/2000 | Alkayali |
| 6,476,005 | B1 | 11/2002 | Petito et al. |
| 6,780,841 | B2 | 8/2004 | Ishaq |
| 6,800,299 | B1 | 10/2004 | Beaudoin et al. |
| 6,806,259 | B2 | 10/2004 | Udell et al. |
| 7,241,463 | B2 | 7/2007 | Nielsen |
| 7,247,752 | B2 | 7/2007 | Lockwood et al. |
| 8,030,037 | B2 | 10/2011 | Thomas et al. |
| 8,481,072 | B2 | 7/2013 | Minatelli et al. |
| 8,524,980 | B2 | 9/2013 | Minatelli et al. |
| 8,557,275 | B2 | 10/2013 | Minatelli et al. |
| 8,586,104 | B2 | 11/2013 | Minatelli et al. |
| 8,591,912 | B1 | 11/2013 | Kadam et al. |
| 8,652,544 | B2 | 2/2014 | Minatelli et al. |
| 8,784,904 | B2 | 7/2014 | Minatelli et al. |
| 8,848,604 | B2 | 9/2014 | Hallaraker et al. |
| 8,945,608 | B2 | 2/2015 | Minatelli et al. |
| 8,962,924 | B2 | 2/2015 | Minatelli et al. |
| 2003/0078304 | A1 | 4/2003 | Andersson et al. |
| 2003/0091652 | A1 | 5/2003 | Ishaq |
| 2003/0096794 | A1 | 5/2003 | Niehoff |
| 2004/0180025 | A1 | 9/2004 | Long et al. |
| 2004/0180851 | A1 | 9/2004 | Long et al. |
| 2004/0234587 | A1 | 11/2004 | Sampalis |
| 2004/0241249 | A1 | 12/2004 | Sampalis |
| 2006/0078625 | A1 | 4/2006 | Rockway |
| 2006/0183709 | A1 | 8/2006 | Alkayali |
| 2007/0098808 | A1 | 5/2007 | Sampalis |
| 2007/0196894 | A1 | 8/2007 | Sim et al. |
| 2007/0270376 | A1 | 11/2007 | Chandler |
| 2008/0014282 | A1 | 1/2008 | Long et al. |
| 2008/0038780 | A1 | 2/2008 | Stocks et al. |
| 2008/0166779 | A1 | 7/2008 | Thomas et al. |
| 2009/0061067 | A1 | 3/2009 | Tilseth et al. |
| 2009/0170808 | A1 | 7/2009 | Ling et al. |
| 2009/0181114 | A1 | 7/2009 | Minatelli et al. |
| 2009/0181127 | A1 | 7/2009 | Minatelli et al. |
| 2009/0258081 | A1 | 10/2009 | Minatelli et al. |
| 2010/0143571 | A1 | 6/2010 | Breivik |
| 2010/0236137 | A1 | 9/2010 | Wu et al. |
| 2010/0291053 | A1 | 11/2010 | Clayton et al. |
| 2011/0020316 | A1 | 1/2011 | Minatelli et al. |
| 2011/0117207 | A1 | 5/2011 | Minatelli et al. |
| 2011/0195061 | A1 | 8/2011 | Minatelli et al. |
| 2011/0268811 | A1 | 11/2011 | Minatelli et al. |
| 2013/0059768 | A1 | 3/2013 | Hallaraker et al. |
| 2013/0287756 | A1 | 10/2013 | Minatelli et al. |
| 2014/0199342 | A1 | 7/2014 | Minatelli et al. |
| 2015/0182552 | A1 | 3/2015 | Minatelli et al. |

FOREIGN PATENT DOCUMENTS

| | | |
|---|---|---|
| EP | 1724357 | 11/2006 |
| GB | 2 103 088 | 2/1983 |
| IN | 201526 | 2/2007 |
| JP | 2005521629 | 7/2005 |
| WO | 03/027267 | 4/2003 |
| WO | 2004/080388 | 9/2004 |
| WO | 2004/112776 | 12/2004 |
| WO | 2011/062953 | 5/2011 |
| WO | 2013/032333 | 3/2013 |
| WO | 2014/013335 | 1/2014 |
| WO | 2014/014766 | 1/2014 |

OTHER PUBLICATIONS

Balogh et al., "Absorption, Uptake and Tissue Affinity of High-Molecular-Weight Hyaluronan After Oral Administration in Rats and Dogs," Journal of Agricultural and Food Chemistry, published Oct. 30, 2008, pp. 10582-10593.

Gotoh et al., "Effects of the Molecular Weight of Hyaluronic Acid and its Action Mechanisms on Experimental Joint Pain in Rats," Annal of the Rheumatic Diseases, 1993, 52:817-822.

Mendes-Pinto et al., "Evaluation of Different Cell Disruption Processes on Encrysted Cells of Haematococcus Pluvialis: Effects on Astaxanthin Recovery and Implications for Bio-Availability," Journal of Applied Phycology, vol. 13, No. 1, Feb. 2001, pp. 19-24.

Nobre et al., "Supercritical Carbon Dioxide Extraction of Astaxanthin and Other Carotenoids from the Microaiga Haematococcus Pluvialis," European Food Research and Technology, vol. 223, No. 6, Mar. 2006, pp. 787-790.

Valderrama et al., "Extraction of Astaxantine and Phycocyanine from Microalgae with Supercritical Carbon Dioxide," Journal of Chemical and Engineering Data, vol. 48, No. 4, Jul. 2003, pp. 827-830.

Mendes et al., "Applications of Supercritical CO2 Extraction to Microalgae and Plants," Journal of Chemical Technology and Biotechnology, vol. 62, No. 1, Jan. 1995, pp. 53-59.

(56) References Cited

OTHER PUBLICATIONS

Calder, "Polyunsaturated Fatty Acids and Inflammation: Therapeutic Potential in Rheumatoid Arthritis," Current Rheumatology Reviews 2009, vol. 5, No. 4, Nov. 2009, pp. 214-225.

Calder, "Joint Nutrition Society and Irish Nutrition and Dietetic Institute Symposium on Nutrition and Autoimmune Disease PUFA, Inflammatory Processes and Rheumatoid Arthritis," Proceedings of the Nutrition Society, vol. 67, No. 4, Nov. 2008, pp. 409-418.

Hurst et al., "Dietary Fatty Acids and Arthritis," Prostaglandins, Leukotrienes and Essential Fatty Acids, vol. 82, No. 4-6, Apr. 2010, pp. 315-318.

Sales et al., "Fish Oil Supplementation in Rheumatoid Arthritis," Reumatismo, vol. 60, No. 3, Jul. 2008, pp. 174-179.

Kikuchi et al., "Bibliographical Investigation of Complementary Alternative Medicines for Osteoarthritis and Rheumatoid Arthritis," Geriatrics and Gerontology International, vol. 9, No. 1, 2009, pp. 29-40.

Deutsch, "Evaluation of the Effect of Neptune Krill Oil on Chronic Inflammation and Arthritic Symptoms," Journal of the American College of Nutrition, vol. 26, No. 1, pp. 39-47 (2007).

Bunea et al., "Evaluation of the Effects of Neptune Krill Oil on the Clinical Course of Hyperlipidemia," Alternative Medicine Review, vol. 9, No. 4, pp. 420-428 (2004).

Lee et al., "Astaxanthin Inhibits Nitric Oxide Production and Inflammatory Gene Expression by Suppressing lkB Kinase-Dependent NF-kB Activation," Molecules and Cells, Jun. 2003, vol. 16, No. 1, pp. 97-105.

Ohgami et al., "Effects of Astaxanthin on Lipopolysaccharide-Induced Inflammation In Vitro and In Vivo," Investigative Opthalmology & Visual Science, Jun. 2003, vol. 44, No. 6, pp. 2694-2701.

Mummert et al., "Synthesis and Surface Expression of Hyaluronan by Dendritic Cells and Its Potential Role in Antigen Presentation," Journal of Immunology, 2002, pp. 4322-4331.

Termeer et al., "Hyaluronan—Magic Glue for the Regulation of the Immune Response?" Trends in Immunology, vol. 24, No. 3, Mar. 2003, pp. 112-114.

McKee et al., "Hyaluronan Fragments Induced Nitric-Oxide Synthase in Murine Macrophages Through a Nuclear Factor kB-Dependent Mechanism," Journal of Biological Chemistry, vol. 272, No. 12, Mar. 21, 1997, pp. 8013-8018.

Brown et al., "Turnover of Hyaluronan in Synovial Joints: Elimination of Labelled Hyaluronan from the Knee Joint of the Rabbit," Experimental Physiology, 1991, No. 76, pp. 125-134.

Serhan et al., "Resolution of Inflammation: State of the Art, Definitions and Terms," The FASEB Journal, vol. 21, Feb. 2007, pp. 325-332.

Moreland, "Intra-Articular Hyaluronan (Hyaluronic Acid) and Hylans for the Treatment of Osteoarthritis: Mechanisms of Action," University of Alabama at Birmingham, Arthritis Research & Therapy, vol. 5, No. 2, Jan. 2003, pp. 54-67.

Lee et al., "Hyaluronan: A Multifunctional, MegaDalton, Stealth Molecule," Current Opinion in Cell Biology, 2000, pp. 581-586.

Kalman et al., "Effect of a Natural Extract of Chicken Combs with a High Content of Hyaluronic Acid (Hyal-Joint®) on Pain Relief and Quality of Life in Subjects with Knee Osteoarthritis: A Pilot Randomized Double-Blind Placebo-Controlled Trial," Nutrition Journal, Jan. 2008, pp. 1-9.

Necas et al., "Hyaluronic Acid (Hyaluronan): A Review," Veterinami Medicine, vol. 53, 2008, pp. 397-411.

Nishimoto et al., "Effect of Chondroitin Sulfate and Hyaluronic Acid on Gene Expression in a Three-Dimensional Culture of Chondrocytes," Journal of Bioscience and Bioengineering, vol. 100, No. 1, 2005, pp. 123-126.

Yamawaki et al., "Hyaluronan Receptors Involved in Cytokine Induction in Monocytes," Glycobiology, vol. 19, No. 1, 2009, pp. 83-92.

Lee et al., "Production of Astaxanthin by Haematococcus," Chemicals from Microalgae, Ed: Zvi Cohen, Taylor and Francis, UK (1999), pp. 173-195.

Bjerkeng et al., "Bioavailability of all-E-astaxanthin and Z-isomers of Astaxanthin in Rainbow Trout (*Oncorhynchus mykiss*)," Aquaculture, vol. 157, Issues 1-2, Nov. 1997, pp. 63-82; Abstract Only (2 pages).

Yang et al., "Glioma-Associated Hyaluronan Induces Apoptosis in Dendritic Cells via Inducible Nitric Oxide Synthase: Implications for the use of Dendritic Cells for Therapy of Gliomas," Cancer Res.; May 2002; 62(9):2583-91; Abstract Only (2 pages).

Ghosh et al., "Potential Mechanism of Action of Intra-Articular Hyaluronan Therapy in Osteoarthritis: Are the Effects Molecular Weight Dependent?" Semin Arthritis Rheum.; Aug. 2002; 32(1):10-37; Abstract Only (2 pages).

Rooney et al., "Angiogenic Oligosaccharides of Hyaluronan Enhance the Production of Collagens by Endothelial Cells," Journal of Cell Science: May 1993; 105 (Pt 1):213 218; Abstract Only (1 page).

Schiedt et al., "Natural Occurrence of Enantiomeric and Meso-Astaxanthin, 5. Ex Wild Salmon (*Salmo saler* and *Oncorhynchus*)," Helv. Chim. Acta; 1981; 64(2):449-57; Abstract Only (1 page).

Jiang et al., "Hyaluronan in Tissue Injury and Repair," Annu Rev Cell Dev Biology; 2007; 23:435-61; Abstract Only (1 page).

Noble, "Hyaluronan and its Catabolic Products in Tissue Injury and Repair," Matrix Biology; Jan. 2002; 21(1):25-9; Abstract Only (1 page).

Stern et al., "Hyaluronan Fragments: An Information-Rich System," European Journal of Cell Biology; Aug. 2006; 85(8):699-715; Abstract Only (1 page).

Ruff et al., "Eggshell Membrane in the Treatment of Pain and Stiffness from Osteoarthritis of the Knee: A Randomized, Multi-center, Double-blind, Placebo Controlled Clinical Study," Clinical Rheumatology; Journal of the International League of Associations for Rheumatology; vol. 28, No. 8; Apr. 2009; pp. 907-914.

Ruff et al., "Eggshell Membrane: A Possible New Natural Therapeutic for Joint and Connective Tissue Disorders. Results from Two Open-Label Human Clinical Studies," Clinical Interventions in Aging 2009 LNKD-PUBMED: 19554094, vol. 4, May 2009, pp. 235-240.

Ierna et al., "Supplementation of Diet With Krill Oil Protects Against Experimental Rheumatoid Arthritis," BMC Musculoskeletal Disorders, Biomed Central Ltd., vol. 11, No. 1, Jun. 29, 2010, 11 pages.

Bergin et al., "Oral Hyaluronan Gel Reduces Post Operative Tarsocrural Effusion in the Yearling Thoroughbred," Equine Veterinary J, 2006, 38(4):375-378.

Guerin et al., "Haematococcus Astaxanthin: Applications for Human Health and Nutrition," Trends in Biotechnology, 2003, 21 (5):210-216.

Peer et al., "Tumor-Targeted Hyaluronan Hanoliposomes Increase the Antitumor Activity of Liposomal Doxorubicin in Syngeneic and Human Xenograft Mouse Tumor Models," Neoplasia, 2004, 6(4):343-353.

Tou et al., "Krill for Human Consumption: Nutritional Value and Potential Health Benefits," Nutrition Reviews, vol. 65, No. 2, Feb. 2007, pp. 63-77.

Gavio et al. "Grateloupia Turuturu (Halymeniaceae, Rhodophyta) is the Correct Name of the Non-Native Species in the Atlantic Known as *Grateloupia doryphora*," Eur. J. Phycol. (2002), 37: 349-359.

Kagan et al. "Acute Appearance of Fatty Acids in Human Plasma—A Comparative Study Between Polar-Lipid Rich Oil from the Microalgae Nannochloropis Oculata in Krill Oil in Healthy Young Males," as published in Lipids in Health and Disease, 2013, 12:102.

Daniels, Stephen "Glycolipids, salts, and wax esters: GOED's Ismail outlines next generation omega-3 forms to watch" http://www.nutraingredients-usa.com/content/view/print/88201; pp. 3; printed Feb. 17, 2014.

Khozin-Goldberg et al. Biosynthesis of eicosapentaenoic acid (EPA) in the freshwater eustigmatophyte monodus subterraneus (uestigmatophyceae) J.Phycol. 38, 745-756 (2002).

Bjorndal et al., Lipids in Health Disease, 2014, 13:82. http://www.lipidworld.com/content/13/1/82.

(56) References Cited

OTHER PUBLICATIONS

Renstrøm B., G. Borch, O. Skulberg and S. Liaane-Jensen, "Optical Purity of (3S,3'S) Astaxanthin From Haematococcus Pluviatis," Phytochemistry, 20(11):2561-2564, 1981. Abtract Only.

Ivonne Pasquali-Ronchetti et al., "Hyaluronan-Phospholipid Interactions", Journal of Structrual Biology 120, pp. 1-10 (1997) Article No. SB973908.

Tsutomo Kawano et al., "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis", Arthritis & Rheumatism vol. 48, No. 7, Jul. 2003, pp. 1923-1929.

Si-Ling Huang et al., "Oral Absorption of Hyaluronic Acid and Phospholipids Complexes in Rats," World Journal of Gastroenterology, Feb. 14 2007, 13(6): pp. 945-949.

Bloomage Freda Biopharm Co., Ltd., The Leader in Sodium Hyaluronate Industry, "HAPLEX © Food Grade HA", Bloomage Bio Technology Corporation Limited, 2014, p. 1.

Andrewes A. and M. Starr entitled, "(3R,3'R)-Astaxanthin from the Yeast Phaffia Rhodozyma," Phytochemistry, 15:1009 1011, 1976. Abstract Only.

Turujman, S, W. Warner, R. Wei and R. Albert entitled, "Rapid Liquid Chromatographic Method to Distinguish Wild Salmon From Aquacultured Salmon Fed Synthetic Astaxanthin," J. AOAC Int, 80(3): 622-632, 1997. Abstract Only.

Schiedt, K., S. Bischof and E. Glinz entitled, "Metabolism of Carotenoids and in vivo Racemization of (3S,3'S)-Astaxanthin in the Crustacean Penaeus," Methods in Enzymology, 214:148-168, 1993. Abstract Only.

Østerlie, M., B. Bjerkeng and S. Liaan-Jensen, entitled "Plasma Appearance and Distribution of Astaxanthin E/Z and R/S Isomers in Plasma Lipoproteins of Men After Single Dose Administration of Astaxanthin," J. Nutr. Biochem, 11:482-490, 2000. Abstract Only.

Coral-Hinostroza, G., T. Ytestøyl, B. Ruyter and B. Bjerkeng entitled, "Plasma Appearance of Unesterified Astaxanthin Geometrical E/Z and Optical R/S Isomers in Men Given Single Doses of a Mixture of Optical 3 and 3'R/S Isomers of Astaxanthin Fatty Acyl Diesters," Comp. Biochem Phys. C., 139:99-110, 2004, Abstract Only.

Katawczik, Melanie "pythium irreguiare" 2008: NC STate University; College of Agriculture and Life Sciences—Department of Plant Pathology, pp. 1-6.

Maharjan et al. "High and low molecular weight hyaluronic acid differentially regulate human fibrocyte differentaiation", PloS One, 2011, 6(10): 1-10.

Itano et al., "Three isoforms of Mammalian Hyaluronan Syntheses Have Distinct Enzymatic Properties," The Journal of Biological Chemistry, vol. 274, No. 35, Aug. 27, 1999; pp. 25085-25092.

Serhan et al., "Resolution of Inflammation: State of the Art, Definitions and Terms," The FASEB Journal, vol. 21, Feb. 2007; pp. 325-332.

Goldberg et al., "Intra-Articular Hyaluronans: The Treatment of Knee Pain in Osteoarthritis," Journal of Pain Research, 2010:3; pp. 51-56.

Nuno et al., "Effects of the Marine Microalgae Isochrysis Galbana and Nannochloropsis Oculata in Diabetic Rats," Journal of Functional Foods, vol. 5, No. 1, Jan. 2013, pp. 106-115.

Capelli et al., "Astaxanthin—Natural Astaxanthin: King of the Carotenoids," Published by Cyanotech Corporation, 2008, pp. 1-148.

Khanafari et al., "Extraction of Astaxanthin Esters From Shrimp Waste by Chemical and Microbial Methods," Iran. J. Environ. Health. Sci. Eng., 2007, vol. 4, No. 2, pp. 93-98.

Spiller et al., "Safety of an Astaxanthin-Rich Haematococcus Pluvialis Algal Extract: A Randomized Clinical Trial," Journal of Medicinal Food, vol. 6, No. 1, 2003 pp. 51-56.

Barnett et al., "Treatment of Rheumatoid Arthritis With Oral Type II Collagen," Arthritis & Rheumatism, vol. 41, No. 2, Feb. 1998; pp. 290-297.

Zavan et al., "Hyaluronan Based Porous Nano-Particles Enriched With Growth Factors for the Treatment of Ulcers: A Placebo-Controlled Study," J Mater Sci: Mater Med (2009) 20:235-247.

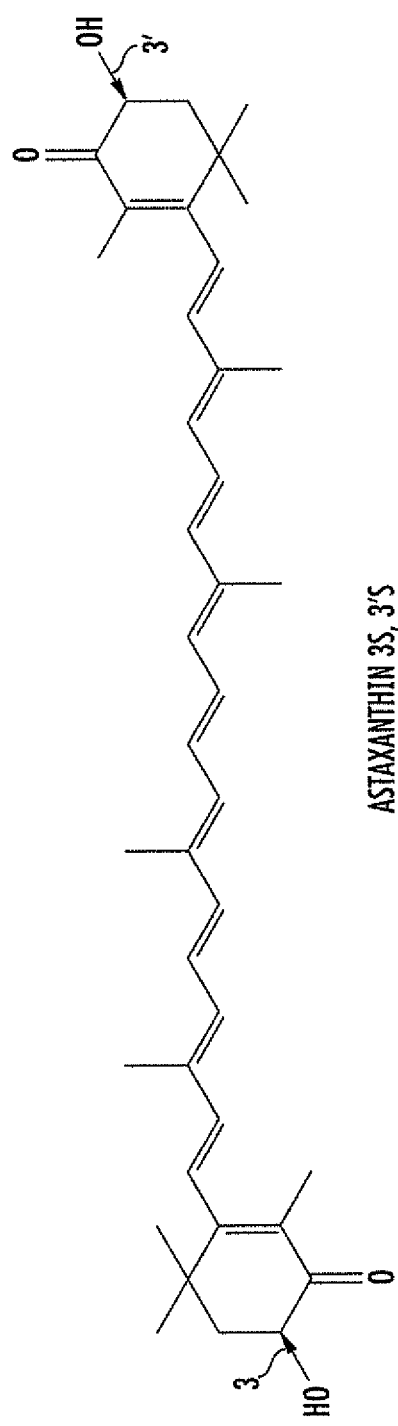

COMPOSITION AND METHOD TO ALLEVIATE JOINT PAIN USING PHOSPHOLIPIDS AND ASTAXANTHIN

RELATED APPLICATION(S)

This is a divisional application of Ser. No. 14/645,890 filed Mar. 12, 2015, which is a continuation-in-part application of Ser. No. 14/217,515 filed Mar. 18, 2014 (now U.S. Pat. No. 9,238,043), which is a continuation-in-part application of Ser. No. 13/914,725 filed Jun. 11, 2013 (now U.S. Pat. No. 8,945,608), which is a continuation application of Ser. No. 12/840,372 filed Jul. 21, 2010 (now U.S. Pat. No. 8,481,072), which is based upon provisional application Ser. No. 61/345,652 filed May 18, 2010; and provisional application Ser. No. 61/227,872 filed Jul. 23, 2009, the disclosures which are hereby incorporated by reference in their entirety.

FIELD OF THE INVENTION

This invention relates to treating and alleviating joint pain and symptoms of osteoarthritis and/or rheumatoid arthritis.

BACKGROUND OF THE INVENTION

The use of krill oil is disclosed in U.S. Patent Publication Nos. 2004/0234587; 2004/0241249; and 2007/0098808, the disclosures which are hereby incorporated by reference in their entirety. The use of krill oil is also disclosed in a research paper published by L. Deutsch entitled, "Evaluation of the Effect of Neptune Krill Oil on Chronic Inflammation and Arthritic Symptoms," published in the Journal of the American College of Nutrition, Volume 26, No. 1, 39-49 (2007), the disclosure which is hereby incorporated by reference in its entirety.

The published '587, '249 and '808 applications discuss the beneficial aspects of using krill oil in association with pharmaceutically acceptable carriers. As an example, this krill and/or marine oil can be obtained by the combination of detailed steps as taught in the '808 application, by placing krill and/or marine material in a ketone solvent, separating the liquid and solid contents, recovering a first lipid rich fraction from the liquid contents by evaporation, placing the solid contents and organic solvent in an organic solvent of the type as taught in the specification, separating the liquid and solid contents, recovering a second lipid rich fraction by evaporation of the solvent from the liquid contents and recovering the solid contents. The resultant krill oil extract has also been used in an attempt to decrease lipid profiles in patients with hyperlipidemia. The '808 publication gives details regarding this krill oil as derived using those general steps identified above.

SUMMARY OF THE INVENTION

Commonly assigned great-grandparent and grandparent U.S. Pat. Nos. 8,481,072 and 8,945,608, and commonly assigned U.S. Pat. No. 8,557,275, which claims priority to the '072 patent, the disclosures which are hereby incorporated by reference in their entirety, are directed to the advantageous use of krill and/or fish derived oils. These patents disclose the beneficial and synergistic effects of alleviating joint pain when krill oil and/or fish derived oil is used in combination with other active constituents such as the low molecular weight hyaluronic acid and astaxanthin. Use of krill oil was one focus in the '072 and '608 patents. A krill or fish derived oil as in the '275 patent as an example includes phospholipid and glycolipid bound EPA (Eicosapentaenoic acid) as compared to fish oils that are triacylglycerides.

Further development had been accomplished with different algae species that produce EPA alone or EPA and DHA (Docosahexaenoic acid). Further development has been accomplished using a roe extract and/or phospholipid sources and/or other surfactants. Further development has also been accomplished when using low molecular weight hyaluronic acid from different sources and with improvements in the use of astaxanthin and making it more bioavailable such as by incorporating a phospholipid or other components.

A dietary supplement composition is formulated in a therapeutic amount to treat and alleviate symptoms of joint pain in a person having joint pain. The composition includes astaxanthin and microbial fermented, low molecular weight hyaluronic acid or sodium hyaluronate (hyaluronan). The composition also includes at least one of a phospholipid, glycolipid, and sphingolipid, and is formulated into an oral dosage form. The astaxanthin is 0.1 to 15 percent by weight of the at least one phospholipid, glycolipid, and sphingolipid.

In an example, the astaxanthin is derived from a natural or synthetic ester or synthetic diol and may include a pharmaceutical or food grade diluent. In another example, the phospholipid comprises at least one of Phosphatidylcholine, Phosphatidylethanolamine, Phosphatidylserine, Phosphatidylinositol, Phosphatidic acid, Lyso-Phosphatidylcholine, Lyso-Phosphatidylethanolamine, and Lyso-Phosphatidylserine. The phospholipid may be derived from at least one of a plant, algae and animal source or synthetic derivatives thereof.

In yet another example, the composition includes 0.5 to 12 mg of astaxanthin and includes 50 to 500 mg of the at least one of the phospholipid, glycolipid and sphingolipid. The dietary supplement composition is formulated into a single dosage capsule in an example. The composition includes pro-inflammatory low molecular weight microbial fermented sodium hyaluronate fragments having a molecular weight of 0.5 to 300 kilodaltons (kDa).

A method to treat and alleviate symptoms of joint pain includes administering to a person having joint pain a therapeutic amount of a dietary supplement composition, including astaxanthin and at least one of a phospholipid, glycolipid, and sphingolipid, and formulated into an oral dosage form. The astaxanthin is 0.1 to 15 percent by weight of the at least one phospholipid, glycolipid and sphingolipid. The composition may be formed by dispersing the astaxanthin under high shear conditions into the at least one phospholipid, glycolipid and sphingolipid.

BRIEF DESCRIPTION OF THE DRAWINGS

Other objects, features and advantages of the present invention will become apparent from the detailed description of the invention which follows, when considered in light of the accompanying drawings in which:

FIG. 1 is a view showing a chemical structure of astaxanthin that can be used in accordance with a non-limiting example.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

There now follows a description of the joint health composition and associated method as set forth in the '072, '608, and '275 patents related to the krill oil and/or fish derived oil and includes novel details of an algae based oil, fish oil derived products, roe and/or plant based oils, including phospholipids, which are more removed from the omega-3 platform base. Novel details and new uses and composition from different hyaluronic acid sources and phospholipids and astaxanthin are described.

The composition as related to the krill oil includes EPA and DHA functionalized as marine phospholipids and acyl-triglycerides derived from krill. The krill, algae, roe extract and fish oil derived product and phospholipid compositions may include astaxanthin, such as esterified astaxanthin, and in one non-limiting example, low molecular weight polymers of hyaluronic acid or sodium hyaluronate (hyaluronan) in an oral dosage form. In one example, it includes pro-inflammatory low molecular weight microbial fermented sodium hyaluronate having a molecular weight of between 0.5 to 300 kDa, in another example between 0.5 to 230 kDa, and in yet another example, between 0.5 to 100 kDa. Some of these components relative to the krill oil in an example are explained in the following chart:

| Components | Percentage (%) |
|---|---|
| PHOSPHOLIPIDS | |
| PC, PE, PI, PS, SM, CL | >40 |
| OMEGA-3 (functionalized on PL) | >30 |
| Eicosapentaenoid Acid (EPA)* | >17 (15% in one example and 10% in another) |
| Docosahexaenoid Acid (DHA)+ | >11 (9% in one example and 5% in another) |
| ANTIOXIDANTS | (mg/100 g) |
| Astaxanthin, Vitamin A, Vitamin E | >1.25 |

*>55% of PL-EPA/Total EPA
+>55% of PL-DHA/Total DHA
These amounts can vary depending on application and persons.

The composition includes pro-inflammatory microbial fermented sodium hyaluronate fragments having a molecular weight of 0.5 to 300 kilodaltons (kDa), in an example, and 0.5 to 230 kDa, and 0.5 to 100 kDa, all in an oral dosage form. Natural high molecular weight hyaluronic acid is the major hydrodynamic component of synovial fluid and importantly is known to be immuno-neutral to the innate immune system. It is nature's bone joint shock absorbent and lubricant. It has been found that there is excellent oral bioavailability of low molecular weight hyaluronic acid (LMWtHA) fragments specifically to connective tissue, which maximizes interaction with target synovial fluid producing cells. Therefore in a preferred composition containing krill oil, algae based oil, fish oil derived product, roe, and phospholipids or other compositions, the astaxanthin and LMWtHA, two anti-inflammatory components are thus combined with one highly inflammatory component.

The scientific literature indicates that LMWtHA fragments exhibit potent pro-inflammatory behavior. It therefore remains unclear why a pro-inflammatory component would elicit a favorable overall response in inflamed joint tissues. It is believed that such pro-inflammatory LMWtHA fragments promote site repair by simulation of the innate immune system repair mechanism and by simulating production of non-immunogenic high molecular weight hyaluronic acid bringing the joint back to homeostasis. A great deal of work by leading immunologists is still attempting to unravel all the aspects of the complicated signaling processes associated with the innate immune system. Studies using large animal models of osteoarthritis have shown that mild immunogenic Hyaluronic Acids with molecular weights within the range of $0.5$-$1.0\times10^6$ Da (Dalton) were generally more effective in reducing indices of synovial inflammation and restoring the rheological properties of SF (visco-induction) than non-immunogenic HA's with molecular weights $>2.3\times10^6$ Da.

Those skilled in the art understand that pro-inflammatory low molecular weight hyaluronic acid is around 300 kDa to about 320 kDa or less, with many skilled in the art using 300 kDa as the cut-off. Low molecular weight hyaluronic acids and sodium hyaluronates are well known to act as pro-inflammatory agents and assumed up-regulators of the inflammatory cascade with respect to the innate immune system. Some reports indicate that hyaluronic acid fragments induce expression of inflammatory genes and they are low molecular weight kDa. Clinical trials by the inventors and their assignee have shown the effectiveness of the composition when using krill oil, together with the low molecular weight hyaluronic acid or hyaluronan and astaxanthin in accordance with a non-limiting example. In the clinical trials, no rescue medication was allowed as compared to the Deutsch study referenced above. The low molecular weight hyaluronic acid had a molecular weight of about 40 kDa in the trial, but could range from 0.5 to 100 kDa in an example, or 0.5 to 230 kDa, or 0.5 to 300 kDa in yet other examples.

The composition and method used in the clinical trials of the current subject matter were directed to treating and alleviating joint pain. The clinical subjects in the clinical trial did not have any confirmed osteoarthritis and/or rheumatoid arthritis. An abbreviated exclusion criteria listed specifically that subjects did not have any presence of auto-immune diseases or similar diseases and the study had excluded those subjects who knew their joint pain was due to osteoarthritis and/or rheumatoid arthritis. The clinical study was directed to patients that have a non-disease state joint pain that is not associated with a disease state such as osteoarthritis and/or rheumatoid arthritis. The composition was used as a supplement to treat and alleviate symptoms of joint pain of unknown etiology, including joint pain not associated with osteoarthritis and/or rheumatoid arthritis in this example.

Astaxanthin is a component of the composition. The clinical trials of the joint care composition with the krill oil, low molecular weight hyaluronic acid and astaxanthin proved the effectiveness of the composition with surprising beneficial results. Related scientific literature indicates that in a lipopolysaccharide induced inflammatory rat model, astaxanthin at just 1 mg/kg in vitro and in vivo: (1) down regulates TNF-alpha production by 75%; (2) down regulates prostaglandin E-2 production (PGE-2) by 75%; (3) inhibits nitric oxide synthase (NOS) expression of nitric oxide by 58%; and (4) these effects on inflammatory markers were nearly as effective as prednisolone in this model. Such information suggests but does not prove that astaxanthin may be an effective standalone product for the reduction of OA and/or RH pain or other symptomology associated with OA and/or RH. FIG. 1 shows an example of the astaxanthin as astaxanthin 3S, 3'S (3,3'-dihydroxy-4,4'-diketo-β-carotene). The clinical trial of 15 mg astaxanthin alone is noted as beneficial.

The incorporated by reference '072 and '608 patents describe that clinical trial using astaxanthin alone where a dosage of one softgel containing 15 mg of astaxanthin as prepared and described was given once a day during breakfast for 12 weeks. This large dosage of astaxanthin alone was effective to treat osteoarthritis and joint pain. It has now been determined that lower dosages of astaxanthin may be used instead of these much higher dosages such as 15 mg in the clinical trial when it is added with at least one of a phospholipid, glycolipid, and sphingolipid or used alone with the low molecular weight hyaluronic acid. A pharmaceutical or food grade diluent may be added or other surfactant. Other beneficial and often synergistic results are obtained when astaxanthin is used in the presence of the low molecular weight hyaluronic acid as described above or UC-II. Phospholipids may include plant based phospholipids such as from lecithin and lysophospholipids and/or glycophospholipids, including *perilla* oil such as described in commonly assigned U.S. Pat. No. 8,784,904, the disclosure which is hereby incorporated by reference in its entirety. Astaxanthin levels could very from 0.5-2 mg and 0.5-4 mg and in one embodiment is 2-4 mg or 2-6 mg and as broad as 0.5-12 mg and 7-12 mg.

In induced uveitis, astaxanthin also showed dose dependant ocular anti-inflammatory activity by suppression of NO, PGE-2 and TNF-Alpha by directly blocking NO synthase activity. Astaxanthin is also known to reduce C-Reactive Protein (C-RP) blood levels in vivo. For example, in human subjects with high risk levels of C-RP three months of astaxanthin treatment resulted in 43% of patients serum C-RP levels to drop below the risk level. This may explain why C-RP levels dropped significantly in the Deutsch study identified above. Astaxanthin is so powerful that it has been shown to negate the pro-oxidant activity of Vioxx, a COX-2 inhibitor belonging to the NSAIDS drug class which is known to cause cellular membrane lipid peroxidation leading to heart attack and stroke. For this reason Vioxx was removed from the US market. Astaxanthin is absorbed in vitro by lens epithelial cells where it suppresses UVB induced lipid peroxidative mediated cell damage at umol/L concentrations. In human trials astaxanthin at 4 mgs/day prevented post exercise joint fatigue following strenuous knee exercise when compared to untreated subjects. These results have been shown in:

1) Lee et al., Molecules and Cells, 16(1):97-105; 2003;
2) Ohgami et al., Investigative Ophthalmology and Visual Science 44(6):2694-2701, 2003;
3) Spiller et al., J. of the Amer. College of Nutrition, 21(5): October 2002; and
4) Fry et al., Univ. of Memphis Human Performance Laboratories, 2001 and 2004, Reports 1 & 2.

A composition in one embodiment includes 300 mg of krill oil, 30 to 45 mg of low molecular weight hyaluronic acid, and 2 mg astaxanthin. It has now been found that 150 mg to 300 mg of krill oil is beneficial with one embodiment using 150 mg. The astaxanthin can range from 0.5 to 2 mg, 2 to 4 mg, 0.5 to 6 mg, 0.5 to 8 mg, 0.5 to 10 mg, 0.5 to 12 mg, and 7 to 12 mg. The use of added phospholipids and/or surfactants described below will aid in delivery of the astaxanthin. The low molecular weight hyaluronic acid can vary from 10 to 70 mg, from 20 to 60 mg, from 25 to 50 mg, with one embodiment having 45 mg, and in another embodiment about 30 mg.

Astaxanthin has potent singlet oxygen quenching activity. Astaxanthin typically does not exhibit pro-oxidant activity unlike β-carotene, lutein, zeaxanthin and Vitamins A and E. Astaxanthin in some studies has been found to be about 50 times more powerful than Vitamin E, 11 times more powerful than β-carotene and three times more powerful than lutein in quenching of singlet oxygen. Astaxanthin is also well known for its ability to quench free radicals. Comparative studies have found astaxanthin to be 65 times more powerful than Vitamin C, 54 times more powerful than β-carotene, 47 times more powerful than lutein, and 14 times more powerful than Vitamin E in free radical quenching ability.

U.S. Pat. No. 5,527,533 (the Tso patent), the disclosure which is hereby incorporated by reference in its entirety, discloses the benefits of astaxanthin for retarding and ameliorating central nervous system and eye damage. Astaxanthin crosses the blood-brain-retina barrier and this can be measured by direct measurement of retinal astaxanthin concentrations. Thus, Tso demonstrated protection from photon induced damage of photo-receptors, ganglion and neuronal cell damage.

Studies have shown that HA binds to the surface of dendritic cells ("DC's") and stimulated T-cells. Blockade of the CD44-HA interaction leads to impaired T-Cell activation both in vitro and in vivo. Studies have shown that in cancer cell lines, LMWtHA fragments specifically induce nitric oxide synthase in dendritic cells. In DC's, NO expression caused dendritic cell apoptosis (cell death). DC's are essential T-cell activators which function by presenting antigens to T-cells, thus apoptosis of DC's may short circuit the adaptive immune system response. This effect was clearly CD44 dependent because pretreatment of DC's with anti-CD44 monoclonal antibodies blocked the NO mediated induction of DC apoptosis. It appears that low molecular weight HA fragments interrupt the normal course of the well known T-cell mediated adaptive immune system response. CD44 is a glycoprotein responsible in part for lymphocyte activation (also known as T-cell activation) and is known to specifically bind to HA. On the other hand as previously discussed low molecular weight HA fragments appear to up-regulate the innate immune response, particularly in chronic inflammatory conditions where the innate immune system may in some way be compromised.

Support for such teachings can be found in:
1) Mummert et al., J. of Immunol. 169, 4322-4331;
2) Termeer at al., Trends in Immunology, Vol. 24, March 2003;
3) Yang et al., Cancer Res. 62, 2583-2591; and
4) McKee et al., J. Biol. Chem. 272, 8013-8018.

Additional information can be found in the following references: Ghosh P. Guidolin D. Semin Arthritis Rheum., 2002 August; 32(1):10-37; and P. Rooney, M. Wang, P. Kumar and S. Kumar, Journal of Cell Science 105, 213-218 (1993).

As noted before, krill oil is typically produced from Antarctic krill (*euphausia superba*), which is a zooplankton (base of food chain). It is one of the most abundant marine biomass of about 500 million tons according to some estimates. Antarctic krill breeds in the pure uncontaminated deep sea waters. It is a non-exploited marine biomass and the catch per year is less than or equal to about 0.02% according to some estimates. Because krill is harvested in large amounts and world supply of krill is being depleted, substitutes for krill such as other marine based oils, including algae based oils, are now being studied, developed and used.

It is believed that krill oil and some other marine based and plant based oils have an oil based phospholipid bound EPA and DHA uptake into cellular membranes that is far more efficient than triacylglyercide bound EPA and DHA, since liver conversion of triacylglycerides is itself inefficient and because phospholipid bound EPA and DHA can be transported into the blood stream via the lympathic system, thus, avoiding liver breakdown. In addition, krill, algae and some marine and plant based oil consumption does not produce the burp-back observed with fish oil based products. Because of this burp-back feature of fish oils, it has been found that approximately 50% of all consumers who try fish oil never buy it again. Some algae based oils have EPA conjugated with phospholipid and glycolipid polar lipids, making the EPA uptake even more efficient.

As to astaxanthin, it has an excellent safety record. A conducted study obtained the results as follows:
Oral LD 50: 600 mg/kg (rats);
NOAEL: 465 mg/kg (rats); or
Serum Pharmacokinetics: Stewart et al. 2008
1) $T_{1/2}$: 16 hours;
2) $T_{max}$: 8 hours;
3) $C_{max}$: 65 µg/L.

At eight weeks of supplementation at 6 mg per day, there was no negative effect in healthy adults. Spiller et al. 2003.

In accordance with one non-limiting example, astaxanthin has three prime sources: 3 mg astaxanthin per 240 g serving of non-farmed raised salmon or a 1% to 12% astaxanthin oleoresin or 1.5-2.5% beadlet derived from microalgae. Further verification is reflected in Lee et al., Molecules and Cells 16(1): 97-105, 2003; Ohgami et al., Investigative Ophthalmology and Visual Science 44(6): 2694-2701, 2003; Spiller et al., J. of the American College of Nutrition 21(5): October 2002; and Fry et al., University of Memphis, Human Performance Laboratories, 2001 and 2004, Reports 1 and 2.

Beneficial and synergistic effects are now being reported herein and have been observed when krill, algae, fish oil derived product, roe extract, and seed oil and other phospholipid based compositions are used in combination with other active ingredients. More particularly, the current composition has krill, algae, fish oil derived, roe, seed oil, or other phospholipid ingredients in combination with astaxanthin and low molecular weight polymers of hyaluronic acid or sodium hyaluronate in preferably an oral dosage form for the control of joint pain range of motion and stiffness. It should be understood that different proportions of the composition components and their percentages can be used depending on end use applications and other environmental and physiological factors when treating a patient.

In accordance with a non-limiting example, the composition and method treats and alleviates symptoms of non-disease state joint pain and may be used to treat and alleviate symptoms of osteoarthritis and/or rheumatoid arthritis in a patient by administering a therapeutic amount of the composition, including the krill oil or other algae based oil, fish oil derived product, roe, and other phospholipid materials in combination with astaxanthin and low molecular weight polymers of hyaluronic acid or sodium hyaluronate (hyaluronan) in an oral dosage form, preferably the low molecular weight polymers. The krill oil alone, in one example, is derived from *Euphasia* spp., comprising Eicosapentaenoic (EPA) and Docosahexaenoic (DHA) fatty acids in the form of triacylglycerides and phospholipids, although not less than 1% EPA and 5% DHA has been found advantageous.

In another example, the krill oil includes at least 15% EPA and 9% DHA, of which not less than 45% are in the form of phospholipids, and in another example 40%. The composition can be delivered advantageously for therapeutic results with 1-4000 mg of oil, such as krill or algae based oil, delivered per daily dose. In another example, 500 mg is a preferred amount for a single capsule dosage, and in another example 1,000 mg. In another example, 0.1-50 mg astaxanthin are supplemented to the oil per daily dose, but a preferred amount is about 2-4 mg and 0.5 to 12 mg. The algae and other marine based oils and roe extract with phospholipid and plant based oils and phospholipids may be used. The composition of the algae based oils and their fatty acid profile varies from the fatty acid profiles of krill oil as explained below and shown in the tables. It is possible to also use wax esters and omega-3 salts and ethyl esters.

The composition may also include an n-3 (omega-3) fatty acid rich oil derived from fish oil, algae oil, flax seed oil, or chia seed oil when the n-3 fatty acid comprises alpha-linolenic, stearidonic, eicosapentaenoic or docosapentaenoic acid. The composition may include naturally-derived and synthetic antioxidants that are added to retard degradation of fatty acids and astaxanthin.

Details of a type of CO2 extraction and processing technology (as supercritical CO2 extraction) and peroxidation blocker technology that can be used are disclosed in commonly assigned U.S. Pat. No. 8,652,544; U.S. Pat. No. 8,586,104; U.S. Pat. No. 8,784,904; and U.S. Patent Publication No. 2009/0181114, the disclosures which are hereby incorporated by reference in their entirety.

As noted before, there are beneficial aspects of using krill oil or algae based oil and other oils as described in synergistic combination with other ingredients. It has been determined that a fish oil derived, choline based, phospholipid bound omega-3 fatty acid mixture including phospholipid bound polyunsaturated EPA and DHA is advantageous for joint health when combined with the astaxanthin and low molecular weight hyaluronic acid or hyaluronate. One commercially available example of a mixture of fish oil derived, choline based, phospholipid bound fatty acid mixture including polyunsaturated EPA and DHA is Omega Choline 1520F as a phospholipid, omega-3 preparation, which is derived from natural fish oil and sold by Enzymotec Ltd. One example of such composition is described below:

| Ingredients (g/100 g): | |
|---|---|
| Pure Marine Phospholipids | n.l.t. 15 |
| DHA* | n.l.t. 12 |
| EPA** | n.l.t. 7 |
| Omega-3 | n.l.t. 22 |
| Omega-6 | <3 |
| Analytical Data: | |
| Peroxide value (meq/Kg) | n.m.t. 5 |
| Loss on Drying (g/100 g) | n.m.t. 2 |
| Physical Properties: | |
| Consistency | Viscous Liquid |

*Docosahexaenoic acid
**Eicosapenteanoic acid

The mixture of fish oil derived, choline based, phospholipid bound fatty acid mixture including polyunsaturated EPA and DHA in one example comprises Eicosapentaenoic (EPA) and Docosahexaenoic (DHA) fatty acids in the form of triacyiglycerides and phospholipids. In another example, the omega choline includes at least 7% EPA and 12% DHA, of which not less than 15% are in the form of phospholipids. The composition can be delivered advantageously for therapeutic results with 1-4000 mg of a mixture of fish oil and fish oil derived, choline based, phospholipid bound fatty acid mixture including polyunsaturated EPA and DHA delivered per daily dose. In one example, about 150 mg to about 300 mg is used. In another example, 2 to 4 mg astaxanthin are supplemented to the omega choline per daily dose, but may include a range of 0.5 to 4 mg, or 0.5 to 6 mg, 0.5 to 12 mg, or 7 to 12 mg, and other ranges as described before.

It is also possible to use a mixture of fish oil derived, choline based, phospholipid bound omega-3 fatty acid mixture (including polyunsaturated EPA and DHA) mixed with astaxanthin and the low molecular weight hyaluronic acid. It should also be understood that an enriched version of a mixture of fish oil derived, choline based, phospholipid bound fatty acid mixture including polyunsaturated EPA and DHA can be used wherein the fraction of added fish oil diluents has been decreased and the proportion of fish oil derived phospholipids has been increased. This can be accomplished by using supercritical CO2 and/or solvent extractions for selective removal of triacylglycerides from phospholipids such as using the techniques in the incorporated by reference patents. The composition may also include a natural or synthetic cyclooxygenase-1 or -2 inhibitor comprising for example aspirin, acetaminophen, steroids, prednisone, or NSAIDs. The composition may also include a gamma-linoleic acid rich oil comprising Borage (*Borago officinalis* L.) or Safflower (*Carthamus tinctorius* L.), which delivers a metabolic precursor to $PGE_1$ synthesis.

The composition may also include an n-3 (omega-3) fatty acid rich oil derived from fish oil, algae oil, flax seed oil, chia seed oil or *perilla* seed oil wherein the n-3 fatty acid source comprises alpha-linolenic, stearidonic, eicosapentaenoic or docosapentaenoic acid. The composition may include naturally-derived and synthetic antioxidants that are added to retard degradation of fatty acids such as tocopherols, tocotrienols, carnosic acid or Carnosol and/or astaxanthin.

It has been found advantageous to use herring roe extract as the source of phospholipids that may have some EPA and DHA. Synergistic results are obtained and vast improvements seen. One study indicated that phospholipids from herring roe improved phospholipid and glucose tolerance in healthy, young adults as published by Bjorndal et al., Lipids in Health Disease, 2014, 13:82. The pure roe phospholipid may be formed using extraction techniques. It is a honey-like product that is thinned or diluted with fish oil and/or *perilla* oil or other seed or plant oil, in an example.

The specification prior to dilution with fish oil and/or *perilla* oil is as follows:

| Percentage that is phospholipids | 60 |
|---|---|
| Phospholipid mg/g | 600 |
| Phosphatidyl choline portion mg/g | 520 |
| Choline equivalents | 83 |
| Total EPA mg/g (TG & PL bound) | 75 |
| Total DHA mg/g (TG & PL bound) | 195 |
| EPA mg/g bound to phospholipid | 67 |
| DHA mg/g bound to phospholipid | 175 |
| EPA + DHA mg/g bound to phospholipid | 242 |

The herring roe extract is processed in one example using extraction by ethanol. Triacylglycerides are added and ethanol stripped out to have a robust solution. Seed oil, such as the *perilla* seed oil as described in the incorporated by reference '904 patent, may be added back to the ethanol extract before stripping to thin and form a high level phospholipid blend. The roe oil extract may be mixed with fish oil and/or seed oil, such as the *perilla*, or any other marine oil. In an example, the herring egg roe extract is mixed with *perilla* seed oil of at least 1:1 and preferably as high as 6:1 ALA to LA with the concentrate as having at least 50%, and in another example 60% phospholipids, and in another example at least 30%, and in another example 40% triglycerides.

An example composition includes a combination of a roe extract from herring or a phospholipid rich roe extract with phospholipid bound EPA and DHA admixed with seed/fish oil and/or seed oil where the seed oil has a ratio of ALA to LA between 1:1 and 1:6, and optionally including astaxanthin in one example of about 2-4 mg or 0.5 to 12 mg or other ranges as noted above, and the low molecular weight hyaluronic acid, such as described above. The amount of roe egg extract mixed with the seed oil such as *perilla* oil varies and is about 150 to 500 mg, or 300 to 500 mg, or up to 1,000 mg daily dose in one example and may include hyaluronic acid. Other plant based phospholipids may be used, including commercially available lecithins and an egg yolk derivative, including lysophospholipids and glycophospholipids to act as surfactants. It is possible to use sunflower-based phospholipids and natural plant-based oils and natural surfactant extracts. The astaxanthin is enhanced with fats, surfactants, or phospholipids and can be delivered more efficiently with phospholipids and sunflower based and/or the lipophilic *perilla* oil as described before.

In an example, the *perilla* oil is formed as a shelf stable, supercritical, CO2 fluid extracted seed oil derived from a cracked biomass of *perilla frutescens* from GO to 95 percent w/w of PUFAs in a ratio of from 4:1 to 6:1 alpha-linolenic acid (ALA) to linoleic acid (LA). The *perilla frutescens* derived seed oil is made in an example by subjecting the *perilla frutescens* seed to supercritical fluid CO2 extraction to produce a seed oil extract; fractionating the resulting seed oil extract in separate pressure step-down stages for collecting light and heavy fractions of seed oil extract; and separating the heavy fraction from the light fraction to form the final seed oil from the heavy fraction.

Selected antioxidants are included in another example and the *perilla* oil includes a mixture of selected lipophilic and hydrophilic antioxidants. Lipophilic antioxidants can be used either alone or in combination with at least one of: a) phenolic antioxidants including at least one of sage, oregano, and rosemary; b) tocopherol; c) tocotrienol(s); d) carotenoids including at least one of astaxanthin, lutein, and zeaxanthin; e) ascorbylacetate; f) ascorbylpalmitate; g) Butylated hydroxytoluene (BHT); h) Docosapentaenoic Acid (BHA); or i) Tertiary Butyl hydroquinone (TBHQ). A hydrophilic antioxidant or sequesterant may include hydrophilic phenolic antioxidants including at least one of grape seed extract, tea extracts, ascorbic acid, citric acid, tartaric acid, and malic acid.

In one example, a peroxide value of this *perilla* seed oil is under 10.0 meq/Km. In another example, this *perilla* seed oil is from 85 to 95 percent w/w of PUFAs and the PUFAs are at least greater than 56 percent alpha-linolenic acid (ALA). The *perilla* seed oil is shelf stable at room temperature up to 32 months. In another example, this *perilla* seed oil is derived from a premilled or flake-rolled cracked biomass of *perilla frutescens*. The mixture of selected antioxidants may include astaxanthin, phenolic antioxidants and natural tocopherols. The *perilla* seed oil may also include at least one of dispersed nano- and micro-particles of rice or sugar cane based policosanol.

In an example, the composition is encapsulated into a single dosage capsule and referred to as a deep ocean caviar capsule. In a specific example, the encapsulated composition includes herring caviar phospholipid extract (herring roe) perilla (perilla frutescens) seed extract, olive oil, Zanthin® astaxanthin (Haematococcus pluvialis algae extract), gelatin, spice extract, non-GMO natural tocopherols, cholecalciferol, riboflavin, and methylcobalamin. The composition includes fish as herring roe and tilapia gelatin. An example is set forth in the following chart.

Properties:

| Appearance - Size 00 clear capsule with dark red oily fill | |
|---|---|
| Fatty Acids | |
| ALA | min. 140 mg |
| EPA | min. 18 mg |
| DHA | min. 50 mg |
| Total Omega-3 | min. 210 mg |
| Phospholipids | 195 mg |
| Astaxanthin | 500 µg |
| Vitamin $D_3$ | 1000 IU; 250% DV |
| Vitamin $B_2$ (Riboflavin) | 1.7 mg; 100% DV |
| Vitamin $B_{12}$ | 6 µg; 100% DV |
| Microbiological | USP <61>/FDA BAM |
| Total Plate Count | <1000 cfu/g |
| Yeast & Mold | <100 cfu/g |
| E. coli | Absent in 10 g |
| Salmonella | Absent in 10 g |
| S. aureus | Absent in 10 g |
| Storage | |
| Conditions | Tightly closed containers, 15-30° C., 30-50% RH |
| Shelf-life | 24 months minimum |
| Packaging | HDPE or PET bottle (count TBD) |

All ingredients BSE-free and non-GMO

The processing components may contain a mix of marine omega-3 phospholipids derived from herring caviar and perilla seed oil. It may contain an O2B™ botanical peroxidation blocker, including spice extract, non-GMO tocopherols and ascorbyl palmitate. It can be packaged as a bulk product in sealed drums 45 and 190 kg net with inert headspace, complying with European and American standards for food products. It preferably stores at below room temperature. The product is protected against light and heat. If drums are opened for sampling, the headspace can be flushed with inert gas during sampling and prior to storing.

| Test | Unit | Acceptance Criterion | | Method |
|---|---|---|---|---|
| Appearance | | Amber viscous oil | | AM2020 |
| Solubility | | Oil soluble and water dispersible | | AM2021 |
| | | Minimum | Maximum | |
| ALA (C18:3 n-3) | mg/g as TG[3] | 230 | | AM1044 |
| EPA (C20:5 n-3) | mg/g as TG[3] | 30 | | AM1001 |
| DHA (C22:6 n-3) | mg/g as TG[3] | 85 | | AM1001 |
| Total omega-3[1] | mg/g as TG[3] | 370 | | AM1001 |
| ALA (C18:3 n-3) | mg/g as FFA[4] | 215 | | AM1044 |
| EPA (C20:5 n-3) | mg/g as FFA[4] | 28 | | AM1001 |
| DHA (C22:6 n-3) | mg/g as FFA[4] | 80 | | AM1001 |
| Total omega-3[1] | mg/g as FFA[4] | 335 | | AM1001 |
| Total PC | mg/g | 250 | | AM1002 |
| Total PL | mg/g | 300 | | AM1002 |
| Total neutral lipids | mg/g | | 700 | AM1003 |
| Water content by Karl Fisher | % | | 3.0 | AM1004 |
| Peroxide value | meq/kg | | 10.0 | AM1005 |
| Heavy metals (sum of Pb, Hg, Cd & In-organic As)[2] | mg/kg | | 10 | AM1015 |

[1] Total n-3: ALA, EPA, DHA, 18:4, 20:4, 21:5, 22:5
[2] Frequency analysis
[3] All ALA, EPA, DHA or Total omega-3 expressed as triglycerides
[4] All ALA, EPA, DHA or Total omega-3 expressed as free fatty acids It has been surprisingly found that the astaxanthin may be made more bioavailable when incorporated or used with one of at least a phospholipid, glycolipid, and sphingolipid and optionally with food and/or pharmaceutical grade diluents. Lower dosages as compared to the 15 mg used in previous clinical trials may be used. The astaxanthin is at least about 0.1 to about 15 percent by weight of the at least one phospholipid, glycolipid, and sphingolipid. The astaxanthin in an example is derived from a natural or synthetic ester or synthetic diol. A pharmaceutical or food grade diluent may be added. When incorporated with a microbial fermented, low molecular weight hyaluronic acid or sodium hyaluronate (hyaluronan) as described before, a dietary supplement composition is formed and can be formulated in a therapeutic amount to treat and alleviate symptoms of joint pain in a person having joint pain.

It should be understood that the triglycerides have two types of molecules as a glycerol and three fatty acids, while the phospholipids contain glycerol and fatty acids, but have one glycerol molecule and two fatty acid molecules. In place of that third fatty acid, a polar group is instead attached to the glycerol molecule so that the phospholipids are partly hydrophilic as compared to hydrophobic triglycerides. Lysophospholipids may be used as a derivative of a phospholipid in which one or both acyl derivatives have been removed by hydrolysis. Lecithin and its derivatives may be used as an emulsifier and surfactant as a wetting agent to reduce surface tension of liquids. Other phospholipids may be used. Different phospholipids include phosphatidylcholine, phosphatidylethanolamine, phosphatidylserine, phosphatidylinositol, phosphatidic acid, lyso-phosphatidylcholine, lysophosphatidylethanolamine, and lyso-Phosphatidylserine. Some may be derived from egg yolk and extracted chemically using hexane, ethanol, acetone, petroleum ether or benzene, and also extracted mechanically, including from different sources such as soybeans, eggs, milk, marine sources, and sunflower. When derived from soya and sunflower, phospholipids may include those products mentioned before, including phosphatidic acid. Various compositions such as lecithin may be hydrolyzed enzymatically and have a fatty acid removed by phospholipase to form the lysophospholipids that can be added to the roe extract as explained above. One phospholipase is phospholipase A2 where the fatty acid is removed at the C2 position of glycerol. Fractionation may be used.

The glycolipids are primarily derivatives of ceramides where a fatty acid is bonded or connected to the amino alcohol sphingosine. It should be understood that the phospholipid sphingomyelin is also derived from a ceramide. Glycolipids, however, contain no phosphates in comparison to the phospholipids. The fat is connected to a sugar molecule in a glycolipid and are fats bonded to sugars. Because it is built from a sphingosine, fat and sugar, some refer to it as a glycosphingolipid. A sphingolipid is a lipid that contains a backbone of sphingoid basis and set of alphatic amino alcohols that include the sphingosine. As noted before, the phospholipid and other components may be derived from at least one of a plant, algae and animal source, or a synthetic derivative thereof. The phospholipid and other components may be derived from at least one of soybean, sunflower, grapeseed, egg yolk, krill, fish body, fish roe, squid, and algae. The phospholipid and other components may be formed as compound rich mono- or di-glcerides or fatty acids where the fatty acid contains between 2 and 20 carbon atoms. During processing, the composition is formed by dispersing the astaxanthin and phospholipid and optionally a diluent under high shear conditions. The diluent may be a pharmaceutical or food grade diluent as known to those skilled in the art.

In another example, the astaxanthin is about 2 to about 10 percent by weight of the phospholipid and glycolipid and derived from a natural or synthetic ester or synthetic diol. In yet another example, 50 to 500 mg of phospholipid, glycolipid, and sphingolipid may be used. The dietary supplement composition may be formulated into a single dosage capsule.

The astaxanthin may be derived from *Haematococcus pluvialis* algae, *Pfaffia*, krill, or by synthetic routes, in the free or synthetic diol, monoester or diester form, both natural and synthetic, at a daily dose of 0.5-8 mg or 0.5-12 mg, in one example, and in another example, 1-2 mg, 2-4 mg, 1-6 mg, and other ranges, and up to 12 mg, including 7-12 mg. The polymers of hyaluronic acid or sodium hyaluronate (hyaluronan) can be derived from microbial fermentation or animal tissue. About 1-500 mg of hyaluronan can be delivered per daily dose and preferably between 10 and 70 mgs/dose and at 20 to 60, 25 to 50, and 35 and 45 mg per dose. The hyaluronan is micro- or nano-dispersed within the composition in one preferred example. In another example, the hyaluronic acid is derived from a biofermenation process and has a molecular weight between 0.5 and 100 kilodaltons (kDa), and in another example, up to 300 kDa and preferably 0.5 to 300 kDa, and in another example, from 0.5 to 230 kDa as low molecular weight hyaluronic acid or hyaluronan. A preferred range is 0.5 to 300 kDa. In another example, the polymers of hyaluronic acid or sodium hyaluronate (hyaluronan) are derived from microbial fermentation or animal tissue.

The pure low molecular weight hyaluronic acid oligomers in an example are derived principally and practically from microbial fermentation, but could also be derived from hydrolyzed animal tissues. This microbial fermentation process is known to produce extraordinarily pure low molecular sodium hyaluronate free from amino acid conjugation.

Human hyaluronic acid is typically synthesized in the body naturally or taken from the diet such as from chicken, beef, and other natural sources. This natural hyaluronic acid has high molecular weight, i.e., greater than 300 kDa, as compared to microbial fermented sodium hyaluronate that is low molecular weight and defined in the literature as about 0.5 to 300 kDa. The hyaluronic acid naturally found in the body is a polymer of acidified glucuronic acid and N-acetyl-glucosamine, which under physiological pH of about 7.4, exists as free acid, with partial sodium, potassium and ammonium salts. *Streptococcus* in one example is used to ferment the sodium hyaluronate and is a mutant strain. Therefore, the resulting low molecular weight hyaluronic acid is obtained from a mutant strain of *streptococcus* bacteria. The fermentation process is followed by isolation and denaturation of the organism and its proteins with ethanol and heat. This is followed by filtration. The molecular weight is chemically modified with acid aqueous chemical hydrolysis as a chemical reaction. The final product is isolated by ethanol precipitation of the sodium salt and drying to produce pro-inflammatory low molecular weight microbially fermented sodium hyaluronate fragments.

This low molecular weight sodium hyaluronate is a chemical reaction degradation product of a mutant strain *streptococcus* bacterial fermentation. An example sodium hyaluronate is manufactured by fermentation using the bacterial strain *streptococcus zooepidemicus*. The production strain is a non-hemolytic mutant of a parent strain, NCTC 7023. The production strain is produced by nitroso-guanidine mutagenesis with a unique ribosomal genome sequence not naturally found in nature.

This manufacturing process has three main stages of 1) fermentation, 2) purification, and 3) refining. The fermentation begins with a seed culture from the mutant production strain. A starter culture inoculates the seed tank, which contains a broth medium that is grown out to become the seed broth. The seed broth is transferred to a fermenter containing the sterilized culture medium and a culturing temperature of 33-37 degrees Celsius is maintained until fermentation is complete within 22-30 hours.

This fermentation broth is mixed with ethanol to obtain precipitated, crude sodium hyaluronate. The 50-70% ethanol concentration used during purification inactivates the *streptococcus* organism. The crude product is dissolved in purified water and filtered to remove both impurities and inactivated microbial fragments. This yields a clear filtrate. The water has a temperature of 50-70 degrees Celsius when used in the dissolution step and inactivates any remaining *streptococcus* organism. The target molecular weight sodium hyaluronate is then obtained by controlling the pH, temperature and holding time in the dissolution step. The higher the pH and temperature in the specified range, and the longer the holding time in the specified range, the lower the resulting molecular weight of the sodium hyaluronate will be. The filtrate containing the chemical hydrolysis derived low molecular weight hyaluronic acid produced during the chemical molecular weight modification step is then precipitated with ethanol, followed by washing or dehydrating. The precipitate is dried under vacuum to yield the final low molecular weight, microbial fermented sodium hyaluronate.

Other sources for low molecular weight hyaluronic acid may be used. These include low molecular weight hyaluronic acid derived from chicken sternal cartilage extract. The hyaluronic acid may include elastin, elastin precursors, and collagen. The hyaluronic acid may be contained in a matrix form with chondroitin sulfate and naturally occurring hydrolyzed collagen Type II nutraceutical ingredients and form lower weight molecules that the body may more readily absorb and deliver to different areas of the body as required. Fresh chicken sternal cartilage could be cut and suspended in aqueous solution followed by treating the cartilage with a proteolytic enzyme to form a hydrolysate. The proteolytic enzyme is capable of hydrolyzing collagen Type II to fragments having a lower molecular weight. The hydrolysate is sterilized and filtered and concentrated and then dried to form powder enriched collagen Type II powder that is then isolated and includes a percentage of low molecular weight hyaluronic acid. Examples of manufacturing techniques can be found in U.S. Pat. Nos. 6,780,841 and 6,025,327, the disclosures which are hereby incorporated by reference in their entirety.

It is possible that the low molecular weight hyaluronic acid could also be derived from the hydrolyzed collagen as derived from the bovine collagen Type T or the chicken sternal cartilage collagen Type II, or even a natural eggshell membrane that includes some hyaluronic acid, which can be extracted from the eggshell membrane. Although some teachings will take the hyaluronic acid derived from eggshell membrane such as in the incorporated by reference patents, the hyaluronic acid is processed to increase its molecular weight using cross-linking techniques as compared to using a low molecular weight hyaluronic acid. The eggshell membrane can still be used to obtain the low molecular weight hyaluronic acid. It may be possible to use enzymatic degradation of eggshell membrane that undergoes manipulation to purify the hyaluronic acid.

The hyaluronic acid may be derived from dehydrated rooster combs such as disclosed in U.S. Pat. No. 6,806,259 and U.S. Patent Publication No. 2006/0183709, which are incorporated herein by reference in their entirety, where the hyaluronic acid may be further processed. Often it is a higher molecular weight and will be processed to obtain a lower molecular weight of the desired 0.5 to 300 kDa. In many teachings, a certain molecular weight hyaluronic acid is processed to increase its molecular weight. The hyaluronic acid may also be obtained from human umbilical cords or other techniques such as disclosed in U.S. Pat. No. 4,141,973, the disclosure which is hereby incorporated by reference in its entirety, and further processed to obtain the desired molecular weight.

It has been determined that synergistic or advantageous improvements can be made to some commercially available compositions that include about 50 mg of an active ingredient, for example, hyaluronic acid and a cartilage, such as a Type II collagen when astaxanthin is added. Sometimes boron is used. For example, the composition includes 30-50 mg of collagen and about 4-6 mg of boron and 2-4 mg of hyaluronic acid with an average of each of the component ranges. It has been found that an effective and synergistic result is obtained when astaxanthin is added alone and/or low molecular weight hyaluronic acid such as 0.5 to 4 mg or 0.5 to 12 mg of astaxanthin plus 30-45 mg of low molecular weight hyaluronic acid, although even smaller amounts could be used, such as 1-5 mg. This composition could include Type II collagen with the added astaxanthin and low molecular weight hyaluronic acid with the optional addition of boron. One (1) to 500 mg of hyaluronic acid could be used.

In an example, a cartilage blend as a mixture of cartilage and salt is about 40 mg with boron as 5 mg and hyaluronic acid as 3.3 mg. The cartilage blend includes cartilage and potassium chloride to provide 10 mg of undenatured Type-2 collagen. It is possible for another composition to include the astaxanthin with the composition that is formed from glucosamine hydrochloride such as about 1.25 to 1.75 or about 1.5 grams and methylsulfonymethane (MSM) of about 500 to 1,000 and about 750 mg and including the addition of chondroitin sulfate of about 150 to 250 and about 200 mg. It also may include the joint fluid as hyaluronic acid, such as 1-5 mg and about 3.3 mg, and also vitamin D3 and other components such as antioxidants. The astaxanthin can vary between 2 to 4 mg or 0.5 to 12 mg and other ranges as disclosed above. It should be understood that the astaxanthin and the at least one of phospholipid, glycolipid, and sphingolipid or other components as described above may be used for many different purposes and results. It may be used to aid in treating or improving blood lipid profiles and reducing LDL per-oxidation in humans. It may be used to counter or treat depression and other neurological disorders. It may be used for respiratory illnesses and skin ailments or diseases.

It has been found advantageous and synergistic to use astaxanthin with low molecular weight hyaluronic acid. It can be incorporated optionally with the UC-II with ranges as described above. Astaxanthin beadlets could be added to the UC-II. This type of composition is advantageous over glucosamine chondroitin pills that require two much larger pills a day to support joint and cartilage. The composition may include a natural or synthetic cyclooxygenase-1 or -2 inhibitor comprising for example aspirin, acetaminophen, steroids, prednisone, or NSAIDs. The composition may also include a gamma-linoleic acid rich oil comprising Borage (*Borago officinalis* L.) or Safflower (*Carthamus tinctorius* L.), which delivers a metabolic precursor to PGE1 synthesis.

The composition may also include an n-3 (omega-3) fatty acid rich oil derived from fish oil, algae oil, flax seed oil, chia seed oil, or *perilla* seed oil. In an example, the n-3 fatty acid comprises alpha-linolenic, stearidonic, eicosapentaenoic or docosapentaenoic acid. In one example composition as noted before, it has been found that an algae based oil may be used instead of krill oil. Hydrolyzed or unhydrolyzed collagen and elastin derived from eggshell membranes can also be advantageously added. The composition may also include anti-inflammatory and/or natural joint health promoting compounds comprising at least one of preparations of green lipped mussel (*Perna canaliculus*), Boswellia serrata, turmeric (*Curcuma longa*), stinging nettle (*Urtica dioica*), Andrographis, Cat's claw (*Uncaria tomentosa*), bromelain, methylsulfonylmethane (MSM), chondroitin sulfate, glucosamine sulfate, s-adenosyl-methionine, proanthocyanidins, procyanidins or flavonoids. The composition may include naturally-derived and synthetic antioxidants that are added to retard degradation of fatty acids and astaxanthin.

Different compositions may use different ingredients in combination with the krill, algae or other oil, including the seed based oil, roe extract, and phospholipid and other surfactants. The astaxanthin and hyaluronate may be combined with different ingredients and supplemental compositions for more specific purposes.

A pharmaceutically acceptable composition comprises a krill, fish, algae, roe extract or plant based oil and/or phospholipid and/or surfactant in combination with astaxanthin and hyaluronate optionally combined with one or more ingredients including but not limited to glucosamine sulfate, chondroitin sulfate, collagen, methylsulfonmethane, a gamma-linoleic acid or omega-3 fatty acid rich oil a cyclooxgenase inhibitor or a lipogenase inhibitor for the treatment of symptoms related to non-disease joint pain and/or joint diseases, including but not limited to osteoarthritis and rheumatoid arthritis.

In yet another example, a dietary supplement acceptable composition comprises a krill, algae, fish, roe extract, or plant based oil and/or other phospholipid and/or surfactant in combination with astaxanthin and hyaluronate optionally combined one or more ingredients, including but not limited to, glucosamine sulfate, chondroitin sulfate, collagen, methylsulfonmethane, a gamma-linoleic acid or omega-3 fatty acid rich oil a cyclooxgenase inhibitor or a lipoxygenase inhibitor for the treatment of symptoms related to non-disease joint pain and/or joint diseases, including but not limited to osteoarthritis and rheumatoid arthritis.

In yet another example, a medical food acceptable composition comprises a krill, algae, fish, roe extract, or plant based oil and/or other phospholipid and/or surfactant in combination with astaxanthin and hyaluronate and optionally combined with one or more ingredients including glucosamine sulfate, chondroitin sulfate, collagen, methylsulfonmethane, a gamma-linoleic acid or omega-3 fatty acid rich oil, a cyclooxygenase inhibitor or a lipoxygenase inhibitor for the treatment of symptoms related to non-disease joint pain and/or joint diseases, including but not limited to osteoarthritis and rheumatoid arthritis.

In still another example, a composition is formulated in a therapeutic amount to treat and alleviate symptoms of non-disease joint pain and/or joint diseases, including osteoarthritis and/or rheumatoid arthritis, wherein the composition includes a krill, algae, fish, roe extract, or plant based oil and/or other phospholipid and/or surfactant in combination with astaxanthin and polymers of hyaluronic acid or sodium hyaluronate (hyaluronan) in an oral dosage form. This composition includes other active constituents as explained and identified above relative to the method and composition.

The composition oil, whether from krill, algae, fish, roe extract, or plant based oil, and/or other phospholipid and/or surfactant, is used with the HA, such as the low molecular weight HA, and astaxanthin to treat non-disease joint pain in one example, but can be used to treat osteoarthritis. Osteoarthritis (OA) is the most prevalent form of arthritis and is a disease in which the cartilage that acts as a cushion between the bones in joints begins to wear away causing bone on bone joint swelling and joint pain. It is characterized by degeneration of articular cartilage along with peri-articular bone response. It affects both sexes, mainly in the fourth and fifth decades of life. The knee joint is most commonly affected joint. At present the management is by pharmacological and non-pharmacological therapy. Corrective surgical therapy and or joint replacement therapy in some cases may not be possible.

Traditional treatments for osteoarthritis involve the use of analgesics, non-steroidal anti-inflammatory drugs (NSAIDs) or cyclooxygenase-2 specific (COX-2) NSAIDs alone or in combination. Advances in recombinant protein synthesis also provide relief from the symptoms of OA and RH. Steroid or high molecular weight hyaluronic acid injections have also been used with some success however these therapies have well known deleterious side effects.

Many of these treatments alone have shown limited effectiveness in clinical trials. To avoid the cardiac risks and gastrointestinal issues associated with traditional OA treatments (particularly with long term use), many patients have turned to complimentary and alternative medicines (CAMs) such as dietary supplements. Glucosamine and chondroitin alone or in combination, are widely marketed as dietary supplements to treat joint pain due to OA. Two major clinical trials on glucosamine and chondroitin (The GAIT Study) failed to show any significant improvement in WOMAC score over placebo except in the highest quartile of patients studied. Because of their limited effectiveness, the search for additional CAMs to treat OA continues (see for example Ruff et al., Eggshell Membrane in the Treatment of Pain and Stiffness from Osteoarthritis of the Knee: A Randomized, Multicenter, Double-Blind, Placebo-Controlled Clinical Study, Clin. Rheumatol (2009) 28:907-914).

It is also possible to use a pure diol of the S, S'astaxanthin, including a synthetic dial with a surfactant and/or the low molecular weight hyaluronic acid. It is possible to use that pure diol in combination with the EPA rich algae based oil or other fish, roe extract, or plant based oil and/or phospholipid and/or surfactant as described above, and which is admixed with either astaxanthin derived from *Haematococcus pluvialis* or the free dial form in substantially pure S,S' enantiomer form. It is possible to add synthetically derived mixed enantiomers of the dial. The diol of the S,S'astaxanthin is possible because in cases of krill oil and possibly algae based oils and Hp derived and other types, there are principally diesters and monoesters respectively with very little diol, which is insoluble. Some research indicates that it may be many times more bioavailable than either the monoester or diester form. It is possible to synthesize asymmetrically the S,S' pure dial. Despite the pure diol's poor solubility in same examples, there may be an active transport mechanism related to its bioavailability, or conversely, that only in the diol form is the monoester or diester forms transferred from the intestines to the blood. The phospholipid or glycolipid based product presenting EPA and/or DHA along with the added astaxanthin in its various forms and especially the S,S' enantiomeric form in principally monoester form from *Haematococcus pluvialis* or pure dial form from asymmetric synthesis could be viable. Thus, it is possible to combine it with the algae derived glycol and phospholipid based EPA rich oil.

As noted before, astaxanthin (3,3'-dihydroxy-β-β-carotene-4,4'-dione) is a xanthophyll carotenoid found in many marine species including crustaceans, salmonid fish and algae. Astaxanthin cannot be synthesized by mammals, but when consumed in the diet has shown effectiveness as an antioxidant, anti-inflammatory agent and with benefit to eye health, heart health, and the immune system.

Astaxanthin has a hydroxyl group on each β-ionone moiety, therefore it can be found in its free (dial) form as well as mono- or di-esterified. In natural products astaxanthin is commonly found as a mixture: primarily mono-esters of C12-C18 fatty acids and lesser amounts of di-ester and free diol. Synthetic astaxanthin is commonly provided in only the free diol form.

The astaxanthin molecule has two E/Z chiral centers and three optical R/S isomers. *Haematococcus pluvialis* algae produces natural astaxanthin solely in the (3S,3'S) isomer. This is explained in the article from Renstrøm B., G. Borch, O. Skulberg and S. Liaane-Jensen, "Optical Purity of (3S, 3'S) Astaxanthin From *Haematococcus Pluvialis*," Phytochemistry, 20(11): 2561-2564, 1981, the disclosure which is hereby incorporated by reference in its entirety.

Alternatively, the yeast *Phaffia rhodozyma* synthesizes only the 3R,3'R configuration. This is explained in the article from Andrewes A. and M. Starr entitled, "(3R,3'R)-Astaxanthin from the Yeast *Phaffia Rhodozyma*," Phytochemistry, 15:1009-1011, 1976, the disclosure which is hereby incorporated by reference in its entirety.

Wild salmon predominately contain the (3S,3'S) form with a (3S,3'S), (3R,3'S), and (3R,3'R) isomer ratio of 22:1:5. This is explained in the article from Turujman, S, W. Warner, R. Wei and R. Albert entitled, "Rapid Liquid Chromatographic Method to Distinguish Wild Salmon From Aquacultured Salmon Fed Synthetic Astaxanthin," J. AOAC Int., 80(3): 622-632, 1997, the disclosure which is hereby incorporated by reference in its entirety.

However, astaxanthin produced by traditional synthesis will contain a racemic mixture in a (3S,3'S), (3R,3'S; meso), (3R,3'R) ratio of 1:2:1. This ratio is also seen in many species of shrimp, which are able to racemize (3S,3'S) to the meso form. This is explained in the article from Schiedt, K., S. Bischof and E. Glinz entitled, "Metabolism of Carotenoids and in vivo Racemization of (3S,3'S)-Astaxanthin in the Crustacean Penaeus," Methods in Enzymology, 214: 148-168, 1993, the disclosure which is hereby incorporated by reference in its entirety.

However, most of the astaxanthin in shrimp is within the carapace (shell) therefore limited amounts of the meso isomer are consumed in the human diet.

Feeding studies of free diol or fatty acid esters of astaxanthin has been shown to increase the amount of astaxanthin in human plasma. This are explained in the article from Østerlie, M., B. Bjerkeng and S. Liaan-Jensen, entitled "Plasma Appearance and Distribution of Astaxanthin E/Z and R/S Isomers in Plasma Lipoproteins of Men After Single Dose Administration of Astaxanthin," J. Nutr. Biochem, 11:482-490, 2000; and the article from Coral-Hinostroza, G., T. Ytestøyl, B. Ruyter and B. Bjerkeng entitled, "Plasma Appearance of Unesterified Astaxanthin Geometrical E/Z and Optical R/S Isomers in Men Given Single Doses of a Mixture of Optical 3 and 3'R/S Isomers of Astaxanthin Fatty Acyl Diesters," Comp. Biochem Phys. C., 139:99-110, 2004, the disclosures which are hereby incorporated by reference in their entirety.

The uptake of free astaxanthin diol is about 4-5 times higher than that of esterified astaxanthin, likely due to the limitation of required enzymatic hydrolysis in the gut prior to absorption. These intestinal enzymes may also be R/S selective on astaxanthin esters. Coral-Hinostroza et al. (2004) found higher relative absorption of astaxanthin from (3R,3'R-astaxanthin dipalmitate compared to the other two isomers. However, ingestion of racemic free diol astaxanthin does not show any stereospecific selection.

Astaxanthin for use in human food supplements is currently derived from the cultivated freshwater algae *Haematococcus pluvialis*. This algae produces 3S,3'S astaxanthin ester in a fatty acid matrix which can be isolated with solvent or carbon dioxide extraction. This oily extract can be used directly in edible formulations or further processed into solid powder or beadlet preparations. Many clinical studies have been conducted with *H. pluvialis* derived astaxanthin to demonstrate beneficial health effects and safety. Food additive approvals for astaxanthin-rich algae extracts have been approved for many suppliers in the US and EU.

*Haematococcus* algae cultivation for use in dietary supplements cannot always match demand for use of astaxanthin in dietary supplements. Use of synthetic astaxanthin diol can also benefit applications which need a concentrated, standardized astaxanthin source. Conventional racemic synthetic astaxanthin sources are used as a colorant in Salmonid aquaculture as a feed ingredient. This racemic mixture may have limited use since only one-quarter of the compound is the 3S,3'S isomer commonly found in natural Salmon and has been studied in humans for efficacy and safety.

Astaxanthin may also be synthesized with in a stereospecific manner, so that the output is exclusively the generally accepted 3S,3'S isomer in a free diol form. The free diol crystals can be suspended in a vegetable oil or solid beadlet for use in edible preparations or pill, capsule, tablet form. The 3S,3'S product has the advantage of greater consistency than algal preparations and also with lower odor. Therefore algal-derived astaxanthin can be replaced with synthetic 3S,3'S astaxanthin diol in existing formulations with the same or increased effectiveness.

As noted before, it has also been surprisingly found that the use of hyaluronic acid alone and/or in combination with astaxanthin is beneficial and synergistic. For example, low molecular weight hyaluronic acid in its different forms can be given to patients in an amount from 1-500 mg per day and preferably about 10-70 mg per day, and in another example, 20-60 mg, 25-50 mg, 35 mg, and 45 mg. Astaxanthin of about 2-4 mg may be added in an example, but could range from 0.5 to 4 mg a day, and 7-12 mg range in another example, or 0.5 to 12 mg. The hyaluronic acid may be given in the form of a pro-inflammatory low molecular weight sodium hyaluronate fragments that are about 0.5-300 kDa corresponding to the pro-inflammatory low molecular weight fragments. Although the use of astaxanthin and phospholipids such as from krill oil, algae oil, roe, fish oil product, or plant based oils helps in delivering the hyaluronic acid, still the low molecular weight hyaluronic acid and in the form of the fragments preferably is still small enough to enter through the gut and be used in an oral administration.

It is also advantageous to use astaxanthin with the low molecular weight hyaluronic acid. Different amounts can be used, and in one example, 2-4 mg per day, and in another example, 0.5-12 mg per day can be used with low molecular weight hyaluronic acid such as the amount of 1-500 mg and preferably about 10-70 mg and with 0.5-12 mg or 4-12 mg of astaxanthin. About 40-120 mg of low molecular weight hyaluronic acid may be used in an example. A dosage of astaxanthin may be about 6-8 mg and the low molecular weight hyaluronic acid could be in the range of about 60-80 mg. Although the greater amounts of astaxanthin may be used with low molecular weight hyaluronic acid alone, it is possible to use 2 mg of astaxanthin and lower amounts of low molecular weight hyaluronic acid such as 20 mg and up to 40 mg as non-limiting examples. It should be understood that hyaluronic acid fragments such as the pro-inflammatory low molecular weight sodium hyaluronate fragments are potent as innate immune system cell receptors signaling molecules associated with the inflammatory cascade and the oral hyaluronic acid in the form of low molecular weight fragments can reach joints as compared to the higher molecular weight hyaluronic acid that is injected since it is not orally administered.

As noted above, algae based oil having been found advantageous in an example. This algae based oil provides an algae sourced EPA or an EPA/DHA based oil in which oils are present in phospholipid and glycerolipid forms, as glycolipids. Different algae based oils derived from different microalgae may be used. One preferred example algae based oil has the EPA titre higher than the DHA as compared to a class of omega-3's from fish oils that are triacylglycerides. These algae based oils are rich in EPA and in the phospholipid and glycolipid forms. An example marine based algae oil is produced by Parry Nutraceuticals as a division of EID Parry (India) Ltd. as an omega-3 (EPA) oil.

It is known that algae can be an important source for omega-3 fatty acids such as EPA and DHA. It is known that fish and krill do not produce omega-3 fatty acids but accumulate those fatty acids from the algae they consume. Omega-3 bioavailability varies and is made available at the site of physiological activity depending on what form it is contained. For example, fish oil contains omega-3 fatty acids in a triglyceride form that are insoluble in water and require emulsification by bile salts via the formation of micelles and subsequent digestion by enzymes and subsequent absorption. Those omega-3 fatty acids that are bound to polar lipids, such as phospholipids and glycolipids, however, are not dependent on bile for digestion and go through a simpler digestion process before absorption. Thus, these omega-3 fatty acids, such as from an algae based oil, have greater bioavailability for cell growth and functioning as compared to the omega-3 triglycerides of fish oil. There are many varieties of algae that contain EPA conjugated with phospholipid and glycolipid polar lipids or contain EPA and DHA conjugated with phospholipids and glycolipids.

Throughout this description, the term "algae" or "microalgae" may be used interchangeably to each other with microalgae referring to photosynthetic organisms that are native to aquatic or marine habitats and are too small to be seen easily as individual organisms with the naked eye. When the term "photoautotropic" is used, it refers to growth with light as the primary source of energy and carbon dioxide as the primary source of carbon. Other forms of biomass that may encompass algae or microalgae may be used and the term "biomass" may refer to a living or recently dead biological cellular material derived from plants or animals. The term "polar" may refer to the compound that has portions of negative and/or positive charges forming negative and/or positive poles. The term "oil" may refer to a combination of fractionable lipid fractions of a biomass. As known to those skilled in the art, this may include the entire range of various hydrocarbon soluble in non-polar solvents and insoluble, or relatively insoluble in water as known to those skilled in the art. The microalgae may also include any naturally occurring species or any genetically engineered microalgae to have improved lipid production.

The following first table shows the specification of an algae based oil as manufactured by Parry Nutraceuticals identified above, followed by a second table for a fatty acid profile chart of that algae based oil. A third table is a comparative chart of the fatty acid profiles for non-algae based oils. These charts show that the algae based oil has a high EPA content of phospholipids and glycolipids.

Specification: Algae Based Oil

| PARAMETERS | SPECIFICATION | SOP. NO | TEST METHOD/ REFERENCE |
|---|---|---|---|
| Physical Properties | | | |
| Appearance | Viscous oil | QA - 88 | In house |
| Color | Brownish black | QA - 88 | In house |
| Odor | Characteristic | QA - 88 | In house |
| Taste | Characteristic | QA - 88 | In house |
| General Composition | | | |
| Loss on drying (%) | 2.0-3.0 | QA - 038 | USP <731> Loss on drying |
| Ash (%) | 0.5-1.0 | QA - 080 | AOAC Official Method 942.05, 16th Edition |
| Protein (%) | 1.0-2.0 | QA - 021 | AOAC Official method 978.04, 16th Edn. |
| Carbohydrate (%) | 1.0-2.0 | | AOAC 18th Edn 2006/By Difference |
| Residual Solvent (ppm) | | QA - 074 | GC - Head Space, USP <467) |
| (as Ethyl Acetate) | NMT 100 | | |
| (as Acetone) | NMT 30 | | |
| Lipid Composition | | | |
| Total Lipid (%) | 92.0-95.0 | QA - 86 | AOAC official method 933.08 |
| Chlorophyll (%) | NMT 1.50 | QA - 078 | Jeffrey & Humphrey (1975) - Photosynthetic pigments of Algae (1989) |
| Total carotenoids (%) | NMT 1.50 | QA - 85 | By JHFA method-1986 |
| Total Unsaponifiables (%) | NMT 12.0 | QA - 086 | AOAC official method 933.08 |
| Omega 3 [EPA + DHA] - % w/w | NLT 15.00 | QA - 087 | In House method |
| Total Omega 3 (% w/w) | NLT 17.00 | | |
| Total Omega 6 (% w/w) | NMT 5.00 | | |
| Total EFA (% w/w) | NLT 20. | | |
| Lipid percentage | | | |
| Triglycerides | 15-20% | | |
| Phospholipids | 5-10% | | |
| Glycolipids | 35-40% | | |
| Free fatty acids | 15-20% | | |
| Microbial parameters | | QA - 039 | AOAC, 1995, Chapter 17 |
| Standard Plate Count (cfu/1 g) | NMT 1,000 | | |
| Yeast & Mold (cfu/1 g) | NMT 100 | | |
| Coli forms (/10 g) | Negative | | |
| E. Coli (/10 g) | Negative | | |
| Staphylococcus (/10 g) | Negative | | |
| Salmonella (/10 g) | Negative | | |
| Fatty acid profile (Area %) | | | |
| Myristic acid [14.0] | NLT 4.0 | QA - 086 & 087 | In House GC method |
| Palmiltic acid [16:0] | NLT 16.0 | | |
| Palmito oleic acid [16:1, n-9] | NLT 12.0 | | |
| Hexadecadienoic acid [16:2, n-4] | NLT 4.0 | | |

| PARAMETERS | SPECIFICATION | SOP. NO | TEST METHOD/ REFERENCE |
|---|---|---|---|
| Hexadecatrienoic acid [16:3, n-4] | NLT 12.0 | | |
| Stearic acid [18:0] | NLT 0.10 | | |
| Oleic acid [18:1] | NLT 1.0 | | |
| Linoleic acid [18:2, n-6] - LA | NLT 1.0 | | |
| Alpha Linolenic acid [18:3, n-3] - ALA | NLT 0.50 | | |
| Stearidonic acid [18:4, n-3] - SA | NLT 0.10 | | |
| Arachidonic Acid [20:4, n-6] - AA | NLT 0.25 | | |
| Eicosapentaenoic acid [20:5, n-3] | NLT 15.0 | | |
| Decosahexaenoic acid [20:6, n-3] | NLT 1.5 | | |
| Heavy Metals | | | |
| Lead (ppm) | NMT 1.0 | External lab reports | AOAC 18th Edn: 2006 By ICPMS |
| Arsenic (ppm) | NMT 0.5 | | |
| Cadmium (ppm) | NMT 0.05 | | |
| Mercury (ppm) | NMT 0.05 | | |

Safety: Safe for the intended use
Shelf life: 24 months from the date of manufacture
Stability: Stable in unopen conditions
Storage: Store in a cool, dry place away from sunlight, flush container with Nitrogen after use
Documentation: Every Batch of shipment carries COA
Packing: 1 kg, 5 kg, and 20 kg food grade containers Fatty Acid Profile Chart Algae Based Oil

| FATTY ACID | ALGAE BASED OMEGA-3 (EPA) OIL |
|---|---|
| Total fatty acid, gm/100 gm of oil | 75 gm |
| Fatty acid [% of total fatty acid] | |
| Myristic acid [14:0] | 6.87 |
| Pentadecanoic acid [15:0] | NA |
| Palmitic acid [16:0] | 20.12 |
| Palmito oleic acid [16:1, ω-9] | 18.75 |
| Hexadeca dienoic acid [16:2, ω-4] | 6.84 |
| Hexadeca trienoic acid [16:4, ω-4] | 12.54 |
| Heptadecanoic acid [17:0] | NA |
| Stearic acid [18:0] | 0.68 |
| Oleic acid [18:1, ω-9] | 3.56 |
| Linoleic acid [18:2, ω-6] | 2.68 |
| Alpha linolenic acid [18:3, ω-3] | 3.73 |
| Gamma linolenic acid [18:3, ω-6] | NA |
| Stearidonic acid [18:4, ω-3] | 0.33 |
| Arachidonic acid [20:4, ω-6] | 0.97 |
| Eicosapentaenoic acid [20:5, ω-3] EPA | 23.00 |
| Docosapentaenoic acid [22:5, ω-3] DHA | NA |
| Docosahexaenoic acid [22:6, ω-3] DHA | 3.26 |
| Others | 3.54 |
| EPA/DHA [gm/100 gm oil] | 15.75 |
| Total ω-3 fatty acids [gm/100 gm oil] | 18.20 |
| LIPD CLASS DETAILS [gm/100 gm oil] | |
| Unsaponifiables [carotenoids, chlorophyll, sterol, fatty alcohol etc.,] | 12 |
| Free fatty acids | 20 |
| Triglydcerides | 20 |
| Phospholipids | 10 |
| Glycolipids | 38 |
| Total | 100 |
| STABILITY [months] | 24 |

Fatty Acid Profile—Comparative Chart

Non-Algae Based Oils

| FATTY ACID | FISH OIL MAXEPA | KRILL OIL | MARTEK OIL |
|---|---|---|---|
| Total fatty acid, gm/100 gm of oil | 95 gm | 70-80 gm | 95 gm |
| Fatty acid [% of total fatty acid] | | | |
| Myristic acid [14:0] | 8.68 | 11.09 | 11.47 |
| Pentadecanoic acid [15:0] | NA | NA | NA |
| Palmitic acid [16:0] | 20.35 | 22.95 | 26.36 |
| Palmito oleic acid [16:1, ω-9] | 11.25 | 6.63 | NA |
| Hexadecadienoic acid [16:2, ω-4] | NA | NA | NA |
| Hexadecatrienoic acid [16:4, ω-4] | NA | NA | NA |
| Heptadecanoic acid [17:0] | NA | NA | NA |
| Stearic acid [18:0] | 4.67 | 1.02 | 0.50 |
| Oleic acid [18:1, ω-9] | 13.07 | 17.93 | 1.50 |
| Linoleic acid [18:2, ω-6] | 1.28 | 0.14 | 0.61 |
| Alpha linolenic acid [18:3, ω-3] | 0.33 | 2.11 | 0.40 |
| Gamma linolenic acid [18:3, ω-6] | NA | NA | NA |
| Stearidonic acid [18:4, ω-3] | 1.69 | 7.01 | 0.33 |
| Arachidonic acid [20:4, ω-6] | 0.50 | NA | NA |
| Eicosapentaenoic acid [20:5, ω-3] EPA | 20.31 | 19.04 | 1.0 |
| Docosapentaenoic acid [22:5, ω-3] DHA | NA | NA | 15.21 |
| Docosahexaenoic acid [22:6, ω-3] DHA | 13.34 | 11.94 | 42.65 |
| others | 4.53 | 0.14 | NA |
| EPA/DHA [gm/100 gm oil] | 31.96 | 21.68 | 41.46 |
| Total ω-3 fatty acids [gm/100 gm oil] | 33.85 | 28.00 | 41.60 |

-continued

| FATTY ACID | FISH OIL MAXEPA | KRILL OIL | MARTEK OIL |
|---|---|---|---|
| LIPD CLASS DETAILS [gm/100 gm oil] | | | |
| Unsaponifiables [carotenoids, chlorophyll, sterol, fatty alcohol etc.,] | 5 | 5 | 5 |
| Free fatty acids | 0.5 | 30 | 0.5 |
| Triglycerides | 94.5 | 25 | 94.5 |
| Phospholipids | Nil | 40 | Nil |
| Glycolipids | Nil | Nil | Nil |
| Total | 100 | 100 | 100 |
| STABILITY [months] | 12 | 24 | 6 |

Different types of marine based algae oils may be used, including *nannochioropsis oculata* as a source of EPA. Another algae that may be used is *thalassiosira weissflogii* such as described in U.S. Pat. No. 8,030,037 assigned to the above-mentioned Parry Nutraceuticals, a Division of EID Parry (India) Ltd., the disclosure which is hereby incorporated by reference in its entirety. Other types of algae as disclosed include *chaetoceros* sp. or *prymnesiophyta* or green algae such as *chlorophyta* and other microalgae that are *diamons tiatoms*. The *chlorophyta* could be *tetraselmis* sp. and include *prymnesiophyta* such as the class prymnesiophyceae and such as the order isochrysales and more specifically, *isochrysis* sp. or *pavlova* sp.

There are many other algae species that can be used to produce EPA and DHA as an algae based oil whether marine based or not to be used in accordance with a non-limiting example. In some cases, the isolation of the phospholipid and glycolipid bound EPA and DHA based oils may require manipulation of the algae species growth cycle.

Other algae/fungi phospholipid/glycolipid sources include: *grateloupia turuturu; porphyridium cruentum; monodus subterraneus; phaeodactylum tricornutum; isochrysis galbana; navicula* sp.; *pythium irregule; nannochloropsis* sp.; and *nitzschia* sp.

Details regarding *grateloupia turuturu* are disclosed in the article entitled, "Grateloupia Turuturu (Halymeniaceae, Rhodophyta) is the Correct Name of the Non-Native Species in the Atlantic Known as Grateloupia Doryphora," Eur. J. Phycol. (2002), 37: 349-359, as authored by Brigitte Gavio and Suzanne Fredericq, the disclosure which is incorporated by reference in its entirety.

*Porphyridium cruentum* is a red algae in the family porphyridiophyceae and also termed rhodophyta and is used as a source for fatty acids, lipids, cell-wall polysaccharides and pigments. The polysaccharides of this species are sulphated. Some *porphyridium cruentum* biomass contains carbohydrates of up to 57%.

*Monodus subterraneus* is described in an article entitled, "Biosynthesis of Eicosapentaenoic Acid (EPA) in the Fresh Water Eustigmatophyte *Monodus Subterraneus* (Eustigmatophyceae)," J. Phycol, 38, 745-756 (2002), authored by Goldberg, Shayakhmetova, and Cohen, the disclosure which is incorporated by reference in its entirety. The biosynthesis of PUFAs from algae is complicated and the biosynthesis from this algae is described in that article.

*Phaeodactylum tricornutum* is a diatom and unlike most diatoms, it can grow in the absence of silicon and the biogenesis of silicified frustules is facultative.

*Isochrysis galbana* is a microalgae and used in the bivalve aquaculture industry.

*Navicula* sp. is a boat-shaped algae and is a diatom. *Pythium irregule* is a soilborne pathogen found on plant hosts.

*Nannochloropsis* sp. occurs in a marine environment, but also occurs in fresh and brackish water. The species are small, nonmotile spheres that do not express any distinct morphological feature. These algae have chlorophyll A and lack chlorophyll B and C. They can build high concentrations of pigment such as astaxanthin, zeaxanthin and canthaxinthin. They are about 2-3 micrometers in diameter. They may accumulate high levels of polyunsaturated fatty acids.

*Nitzschia* sp. is a pinnate marine diatom and usually found in colder waters and associated with both Arctic and Antarctic polar sea ice where it is a dominant diatom. It produces a neurotoxin known as domoic acid which is responsible for amnesic shell fish poisoning. It may grow exponentially at temperatures between −4 and −6 degrees C. It may be processed to form and extrapolate the fatty acids.

As a source of polyunsaturated fatty acids, microalgae competes with other micro-organisms such as fungi and bacteria. There may be some bacterial strains that could be an EPA source, but microalgae has been found to be a more adequate and readily available source. Microalgae is a good source of oil and EPA when derived from *phaeodactylum, isochrysis* and *monodus*. The microalgae *phaeodactylum tricornutum* produces a high proportion of EPA. Other different strains and species of microalgae, fungi and possibly bacteria that can be used to source EPA include the following:

I. Diatoms
  *Asterionella japonica*
  *Bidulphia sinensis*
  *Chaetoceros septentrionale*
  *Lauderia borealis*
  *Navicula biskanteri*
  *Wavicula laevis (heterotrof.)*
  *Navicula laevis*
  *Navicula incerta*
  *Stauroneis amphioxys*
  *Navicula pellicuolsa*
  *Biduiphia aortia*
  *Nitzschia alba*
  *Nitzschia chosterium*
  *Phaeodactylum tricornutum*
  *Phaeodactylum tricornutum*
  *Skeletonema costatum*
II. Chrysophyceae
  *Pseudopedinella* sp.
  *Cricosphaera elongate*
III. Eustigmatophyceae
  *Monodus subterraneus*
  *Nannochloropsis*
IV. Prymnesiophyceae
  *Rodela violacea* 115.79
  *Porphyry. Cruentum* 1380.Id
V. Prasinophyceae
  *Pavlova sauna*
VI. Dinophyceae
  *Cochlodinium heteroloblatum*
  *Cryptecodinium cohnii*
  *Gonyaulax catenella*
  *Gyrodinium cohnii*
  *Prorocentrum minimum*

VII. Other Microalgae
   Chlorella minutissima
   Isochrysis galbana ALII4
   Phaeodactylum tricornutum WT
   Porphyridium cruentum
   Monodus subterraneus
VIII. Fungi
   Mortierella alpine
   Mortierella alpine IS-4
   Pythium irregulare
IX. Bacteria
   SCRC-2738

Different microalgae may be used to form the algae based oil comprising glycolipids and phospholipids and at least EPA and/or EPA/DHA. Examples include: *Chlorophyta*, Cyanophyta (Cyanobacteria), and Heterokontophyta. The microalgae may be from one of the following classes: Bacillariophyceae, Eustigmatophyceae, and Chrysophyceae. The microalgae may be from one of the following genera: *Nannochloropsis, Chlorella, Dunaliella, Scenedesmus, Selenastrum, Oscillatoria, Phormidium, Spirulina, Amphora*, and *Ochromonas*.

Other non-limiting examples of microalgae species that may be used include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Effipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochioris* sp., *Nannochloropsis salina, Nannochioropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricamutum, Phagus, Phormidium, Platymonas* sp., *Pleurochrysis carterae, Pleurochrysis dentate, Pleurochrysis* sp., *Prototheca wickerharnii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana*. Preferably, the microalgae are autotrophic.

It is also possible to form the oil comprising glycolipids and phospholipids and at least EPA from genetically modified yeast. Non-limiting examples of yeast that can be used include *Cryptococcus curvatus, Cryptococcus terricolus, Lipomyces starkeyi, Lipomyces lipofer, Endomycopsis vernalis, Rhodotorula glutinis, Rhodotorula gracilis, Candida 107, Saccharomyces paradoxus, Saccharomyces mikatae, Saccharomyces bayanus, Saccharomyces cerevisiae*, any *Cryptococcus, C. neoformans, C. bogoriensis, Yarrowia lipolytica, Apiotrichum curvatum, T. bombicola, T. apicola, T. petrophilum, C. tropicalis, C. lipolytica*, and *Candida albicans*. It is even possible to use a biomass as a wild type or genetically modified fungus. Non-limiting examples of fungi that may be used include *Mortierella, Mortierrla vinacea, Mortierella alpine, Pythium debaryanum, Mucor circinelloides, Aspergillus ochraceus, Aspergillus terreus, Pennicillium iilacinum, Hensenulo, Chaetomium, Cladosporium, Malbranchea, Rhizopus*, and *Pythium*.

It is also possible that bacteria may be used that includes lipids, proteins, and carbohydrates, whether naturally occurring or by genetic engineering. Non-limiting examples of bacteria include: *Escherichia coli, Acinetobacter* sp. any actinomycete, *Mycobacterium tuberculosis*, any streptomycete, *Acinetobacter calcoaceticus, P. aeruginosa, Pseudomonas* sp., *R. erythropolis, N. erthopolis, Mycobacterium* sp., B., *U. zeae, U. maydis, B. lichenformis, S. marcescens, P. fluorescens, B. subtilis, B. brevis, B. polmyma, C. lepus, N. erthropolis, T. thiooxidans, D. polymorphis, P. aeruginosa* and *Rhodococcus opacus*.

Possible algae sourced, EPA/DHA based oils that are derived from an algae and contain glycol and phospholipid bound EPA and/or EPA/DHA and may include a significant amount of free fatty acids, triglycerides and phospholipids and glycolipids in the range of 35-40% or more of total lipids are disclosed in the treatise "Chemicals from Microalgae" as edited by Zvi Cohen, CRC Press, 1999. Reference is also made to a study in men that have been given a single dose of oil from a polar-lipid rich oil from the algae *nannochloropis oculata* as a source of EPA and described in the article entitled, "Acute Appearance of Fatty Acids in Human Plasma—A Comparative Study Between Polar-Lipid Rich Oil from the Microalgae *Nannochloropis Oculata* in Krill Oil in Healthy Young Males," as published in. Lipids in Health and Disease, 2013, 12:102 by Kagan et al. The EPA in that algae oil was higher than that of krill oil by about 25.06 to 13.63 for fatty acid composition as the percent of oil. The algae oil was provided at 1.5 grams of EPA and no DHA as compared to krill oil that was provided at 1.02 grams EPA and 0.54 grams DHA. The participants consumed both oils in random order and separated by seven days and the blood samples were collected before breakfast and at several time points up to 10 hours after taking the oils.

The researchers determined that the algae based oil had a greater concentration of EPA and plasma than krill oil with the EPA concentration higher with the algae based oil at 5, 6, 8 and 10 hours (P<0.05) intended to be higher at 4 hours (P=0.094). The maximum concentration (CMAX) of EPA was higher with algae oil than with krill oil (P=0.010). The maximum change in concentration of EPA from its fasting concentration was higher than with krill oil (P=0.006). The area under the concentration curve (AUC) and the incremental AUC (IAUC) was greater (P=0.020 and P=0.006). This difference may relate to the different chemical composition and possibly the presence of the glycolipids where the presence of DHA in krill oil limits the incorporation of EPA into plasma lipids. Also, the n-3 polyunsaturated fatty acids within glycolipids as found in the algae oil, but not in a krill oil, may be an effective system for delivering EPA to humans.

Microalgae can be cultured photoautotrophically outdoors to prepare concentrated microalgae products containing Eicosapentaenoic acid (EPA) and Docosahexaenoic acid (DHA), which are the long-chain polyunsaturated fatty acids (PUFAs) found in fish oil. Both are very important for human and animal health. The concentrated microalgae products as disclosed in the '037 patent may contain EPA and DHA and lipid products containing EPA and DHA purified from microalgae. The concentrated microalgae composition may be prepared by cultivating microalgae photoautotrophically outdoors in open ponds under filtered sunlight in a continuous or batch mode and at a dilution rate of less than 35% per day. The microalgae may be harvested in the exponential phase when the cell number is increasing at a rate of at least 20% of maximal rate. In one example, the microalgae is concentrated. In another example, at least 40% by weight of lipids in the microalgae are in the form of glycodiacylglycerides, phosphodiacylglycerides, or a combination thereof and at least 5% by weight of the fatty acids are DHA, EPA, or a combination thereof.

In one example, the microalgae are *Tetraselmis* sp. cultivated at above 20° C. or in another example at above 30° C. The EPA yield in the microalgae has been found to be at least 10 mg/liter culture. The microalgae can be *Isochrvsis* sp. or *Pavlova* sp. in another example, or are *Thalassiosira* sp. or *Chaetecoros* sp. The microalgae may be different diatoms and are cultivated photoautotrophically outdoors in open ponds for at least 14 days under filtered sunlight and at least 20% by weight of the fatty acids are EPA.

The use of this algae based oil overcomes the technical problems associated with the dwindling supplies of fish oil and/or Antarctic krill, which are now more difficult to harvest and obtain and use economically because these products are in high demand. A major difference between fish oils and algae based oils is their structure. Fish oils are storage lipids and are in the form of triacylglycerides. The algae based oils as lipids are a mixture of storage lipids and membrane lipids. The EPA and DHA present in algae based oils is mainly in the form of glycolipids and a small percentage is in the form of phospholipids. Glycolipids are primarily part of chloroplast membranes and phospholipids are part of cell membranes.

The '037 patent describes various methods for culturing microalgae photoautotrophically outdoors to produce EPA and DHA. One method used is filtering sunlight to reduce the light intensity on the photoautotrophic culture. Shade cloth or netting can be used for this purpose. It was determined that for most strains, the optimal solar intensity for growth, for maintaining a pure culture, and for omega-3 fatty acid accumulation was about 40,000 to 50,000 lux, approximately half of the 110,000 lux of full sunlight. Shade cloth or netting is suitable for filtering the sunlight to the desired intensity.

It is also possible to culture microalgae photoautotrophically outdoors and produce EPA and DHA by using small dilutions and a slow dilution rate of less than 40% per day, preferably less than 35% per day, more preferably from about 15% to about 30% per day. In other examples, the dilution rate is 15-40% per day or 15-35% per day, and in yet other examples, the dilution rate is 10-30%, 10-35%, or 10-40% per day. These smaller dilutions and lower dilution rates than are usually used help prevent contamination in outdoor photoautotrophic cultures. It also promotes thick culture growth that gives good DHA or EPA yield.

Another technique to successfully culture microalgae photoautotrophically outdoors and produce EPA and EPA/DHA is to harvest the microalgae in exponential phase rather than stationary phase. Harvesting in exponential phase reduces the risk of contamination in outdoor photoautotrophic cultures and has surprisingly been found to give a good yield of EPA and DHA. To drive fat accumulation in microbial cultures, the cultures are harvested in stationary phase because cells in the stationary phase tend to accumulate storage lipids. The '037 patent teaches that EPA and DHA accumulate in large amounts as membrane lipids in cultures harvested in the exponential phase. The membrane lipids containing EPA and DHA are predominantly phosphodiacylglycerides and glycodiacylglycerides, rather than the triaclyglycerides found in storage lipids. These cultures are harvested often when cell number is increasing at a rate at least 20% of the maximal rate, i.e., the maximal rate achieved at any stage during the outdoor photoautotrophic growth of the harvested culture. In specific examples, the cultures are harvested in exponential phase when cell number is increasing at a rate of at least 30%, at least 40%, or at least 50% of maximal rate. It is also possible to use recombinant DNA techniques.

The '037 patent includes several examples, which are referenced to the reader for description and teaching purposes.

Example 1

The strain *Thalassiosira* sp. is a diatom and this strain used was isolated from Bay of Bengal, and it dominates during summer months. This example strain was isolated from seawater collected near Chemai, India, and the culture was maintained in open tubs. The particular strain was identified as *Thalassiosira weissflogii*, which is capable of growth at high temperatures (35-38° C.). The fatty acid profile was good even when the alga was grown at high temperature with 25-30% EPA (as a percentage of fatty acids).

Culturing:

The lab cultures were maintained in tubs in an artificial seawater medium, under fluorescent lights (3000-4000 lux) and the temperature was maintained at 25° C. Initial expansion of the culture was done under laboratory condition in tubs. The dilution rate was 15% to 30% of the total culture volume per day. Once the volume was 40-50 liters, it was transferred to an outdoor pond. The outdoor ponds were covered with netting to control the light (40,000 to 50,000 lux). The dilution continued until the culture reached 100,000 liters volume. The culture was held in 500 square meter ponds at this time with a culture depth of 20 cm. The culture was stirred with a paddle wheel and CO2 was mixed to keep the culture pH neutral. When the EPA levels in the pond reached a desirable level (10-15 mg/lit), the whole pond was harvested by filtration. The filtered biomass was washed with saltwater (15 parts per thousand concentration) and then spray dried. The mode of culturing was batch mode. The EPA productivity was 2-3 mg/lit/day. The ponds can also be run continuously for several weeks by harvesting part of the culture, recycling the filtrate into the ponds and replenishing required nutrients.

Example 2

The strain *Tetraselmis* sp. is in the division *Chlorophyta* and the class Prosinophyceae or Micromanadophyceae. This strain was obtained from the Central Marine Fisheries Research Institute, India. It was isolated from the local marine habitats in India. The culture was maintained in flasks in artificial seawater medium, and expanded as described for *Thalassiosira*. With culture outdoors in open ponds as described for *Thalassiosira*, the strain gave a good lipid yield (200-300 mg/liter) and an EPA content of 6-7% of fatty acids.

Example 3

The strain *Chaetoceros* sp. is another diatom strain obtained from the Central Marine Fisheries Research Institute, India, and isolated from local marine habitats in India. *Chaetoceros* sp. was maintained in flasks and cultivated in outdoor ponds photoautotrophically as described in Example 1. It gave similar EPA productivity and EPA content as *Thalassiosira* as described in Example 1.

Example 4

The strain *Isochrysis* sp. is in the *Prymnesiophyta*, class Prymnesiophyceae, order Isochrysidales. It was obtained from the Central Marine Fisheries Research Institute, India, and isolated from local marine habitats in India. It was maintained and grown as described in Example 1. It was expanded from laboratory culture to a 50,000 liter outdoor pond culture in 14-15 days with a dilution rate of 15-30% per day. The lipid content at harvest was 100-150 mg lipids/liter. The rate of lipid production was 25-50 mg/liter/day. DHA was 10-12% of total fatty acids.

Example 5

Harvesting and Drying: The harvesting may be done by flocculation. The commonly used flocculants include Alum with polymer and FeCl3 with or without polymer and chitosan. The concentration of flocculent will depend on the cell number in the culture before harvest. The range may vary from 100 ppm to 500 ppm. Alternatively, harvesting is done by filtration using appropriate meshes. Removal of adhered chemicals (other than salt) is accomplished by washing the cells in low salinity water.

The harvested slurry is then taken for spray drying. The slurry is sometimes encapsulated to prevent oxidation. The concentration of encapsulating agent may vary from 0.1 to 1.0% on a dry weight basis. Modified starch is a suitable encapsulating agent. The spray dryer is usually an atomizer or nozzle type. The inlet temperature ranges from 160 to 190° C. and the outlet temperature ranges from 60 to 90° C. The spray dried powder is used immediately for extraction. If storage is required, the powder is packed in aluminum laminated pouches and sealed after displacing the air by nitrogen. The packed powder is stored at ambient temperature until further use.

Example 6

Extraction of EPA/DHA is carried out using a wet slurry or dry powder and solvents, which include hexane, ethanol, methanol, acetone, ethyl acetate, isopropanol and cyclohexane and water, either alone or in combination of two solvents. The solvent to biomass ratio depends on the starting material. If it is a slurry, the ratio is 1:2 to 1:10. With a spray dried powder, on the other hand, the ratio is 1:4 to 1:30. The extraction is carried out in an extraction vessel under inert atmosphere, with temperature ranges from 25 to 60° C. and with time varying from one hour to 10 hours. Solvent addition is made one time or in parts based on the lipid level in the cells.

After extraction of crude lipid, the mixture is passed through a centrifuge or filtration system to remove the cell debris. The lipid in the filtrate is concentrated by removing the solvent by distillation, which is carried out under vacuum. The resulting product is a crude lipid extract, which contains approximately 10% omega-3 fatty acid (EPA/DHA). The extract can be used as it is or purified further to enrich the omega-3 fatty acids. Further purification may involve removal of unsaponifiables such as pigments, sterols and their esters. The algae based oil composition may be used for different purposes as described.

In the incorporated by reference '072 and '608 patents, a clinical trial using astaxanthin alone is described where a dosage of one softgel containing 15 milligrams of astaxanthin was given once a day during breakfast for 12 weeks and 70 subjects recruited for the study. This was a comparative single blind clinical trial and a total of 70 subjects recruited for the study with 35 in each group corresponding to an astaxanthin oleoresin complex and a placebo-control. The clinical trial results are reproduced below and show the efficacy of using high dosages of astaxanthin at levels of 15 mg. It has been found, however, that surprisingly effective results are used when 2 to 4 mg or 0.5 to 12 mg or other ranges as described of astaxanthin are used alone in the presence of an adequate surfactant such as a sunflower or *perilla* based phospholipid. This could include the roe extract with phospholipid as described above. This could be a plant based phospholipid also and a lecithin alone or modified as a lysophospholipid source. It is possible to use glycophospholipids. An example *perilla* oil is described and disclosed in the incorporated by reference and commonly assigned '904 patent. The astaxanthin and surfactant may optionally be admixed with low molecular weight hyaluronic acid as described above or UC-II. The astaxanthin in the presence of a surfactant may be at below 4 mg/day and as noted before, optionally admixed with the low molecular weight hyaluronic acid or UC-II and/or as a chicken sternum collagen isolate. The phospholipid may have little EPA and DHA. In one example, a preferred astaxanthin concentration is about 2-4 mg and a chicken sternum collagen isolate can be about 40 mg and have a range of 30 to about 50 mg. Other surfactants such as plant based phospholipids and commercially available lecithins that are modified and including egg yolk compositions and/or sea based oils such as from *perilla* may be used. Sea based phospholipids and lysolipid, also referred to as lyso-phospholipid, counterparts may be used. A non-omega-3 platform may be used with the current invention. The low molecular weight hyaluronic acid as described may vary from 1-500 mg, 10-70 mg, 35 mg, or 45 mg, and other ranges as described, and is a preferred low molecular weight microbial fermented product as described above.

The clinical trial as set forth in the '072 and '608 patents is now set forth.

Clinical Trial to Evaluate the Efficacy of *Haematococcus Pluvialis* Astaxanthin Oleoresin Complex in Osteoarthritis Patients:

The study has been carried out as a comparative single blind clinical trial of astaxanthin oleoresin complex in 60 Osteoarthritis patients as compared with Placebo control for a period of 12 weeks n=60 (30A+30 P). The dosage consisted of one softgel containing 15 mg of Astaxanthin once a day during breakfast for 12 weeks. A total of 70 subjects were recruited for the study, 35 in each group (Astaxanthin oleoresin complex and placebo-control) of both the sexes. Patients were explained the nature of the study and informed consent was obtained prior to the start of the study. Patient subjects were clinically examined by the Principal Investigator and team. X ray and blood samples were drawn at the commencement and at the end of study period. The case record forms were filled by the Principal Investigator and rechecked by the Clinical research associate. Sixty patient subjects completed the study. Ten were drop outs due to various reasons but not on account of intolerance to the astaxanthin oleoresin complex or placebo control. The results were tabulated by the expert data entry operators under supervision of Biometric expert. The results were subjected to Statistical analysis by an independent analyst.

The assessment of Osteoarthritis symptoms were based on Western Ontario and McMasters Universities (WOMAC) Osteoarthritis Index, VAS scale, Lequesne's functional scale as well as Sleep score as additional parameters besides radiological investigations. Further the assessment of Osteoarthritis symptoms based on haematological studies, specifically MMP3 (Matrix metalloproteinase 3) in clinical parameters since Osteoarthritis patients show elevated levels of MMP3 in blood as well as in synovial fluid. The elevated levels cause significant tissue damage through cartilage destruction.

Results of Clinical Trial and Discussions:

Total Health Assessment Score—The total health assessment on Osteoarthritis patients was carried out on their difficulty to a) Dressing—doing buttons, washing and combing hair; b) Arising—stand up straight from a chair, get in and out of bed, sit cross-legged on floor and get up; c) Eating—cut vegetables, lift a full cup/glass to your mouth; d) Walking—walk outdoor on flat ground, climb up five steps; and e) Hygiene—Take a bath, wash and dry your body, get on and off the toilet; f) Reaching—reach and get down a 2 kg object from just above your head, bend down to pick up clothing from the floor; g) Grip-open a bottle previously opened, turn taps on & off, open door latches; h) Activities-work in office/house, run errand to shop, get in and out of car/auto. The summary of results is given Table 3.

There were significant reductions in the mean scores of patients taking astaxanthin oleoresin complex at the end of 3 months but not for the Placebo group. There were no significant differences between astaxanthin and Placebo group at Basal values. There were significant differences between the astaxanthin and placebo group at 3 months.

WOMAC Score—

The Western Ontario McMaster (WOMAC) is a validated instrument designed specifically for the assessment of lower extremity pain and function in Osteoarthritis (OA) of the knee. The patients were assessed on their pain, stiffness and difficulty in carrying out day-to-day activities. The pain index was assessed for Activities—a) in walking on flat surface, going up or down on flat surface, at night while in bed, sitting or lying, standing upright; b) Stiffness—after first wakening in morning, after sitting/lying or resting later in the day; and c) difficulty in descending stairs, ascending stairs, standing up from a chair, while standing, bending to floor to pick up objects, walking on flat ground, getting in and out of autorickshaw/bus/car, going shopping, on rising from bed, while lying on bed, while sitting on chair, going on/off toilet, doing heavy domestic duties such as moving heavy boxes/scrubbing floor/lifting shopping bags, doing light domestic duties such as cleaning room/table/cooking/dusting, while sitting cross-legged position, rising from cross-legged position, while squatting on floor. The summary of the results are given in Table 4.

There were significant reductions in the mean scores for patients taking Astaxanthin oleoresin complex at the end of 3 months but not for the Placebo group. There were no significant differences between patients taking Astaxanthin oleoresin complex and placebo group at basal values. There were significant differences between Astaxanthin and Placebo groups at 3 months.

VAS (Visual Analog Scale) on Pain Parameters—

Pain parameters were assessed in Osteoarthritis patients taking astaxanthin oleoresin and the Placebo group using VAS. The assessment was carried out in a) Pain parameters—pain while using stairs, pain while walking on flat ground, pain while standing upright, pain while sitting or lying down, pain at night in bed b) Physical functions—going downstairs, going upstairs, sitting, getting up from sitting, standing, bending to floor, walking on flat ground, getting into or out of automobiles, shopping, putting on socks/stockings, taking off socks/stockings, getting into bed, getting out of bed, getting into or out of bath tub, getting on or off toilet seat, during heavy household chores, during light household chores, getting into lotus position. The summary of results of Pain parameters (Pain+Physical) scores are given in Table 5.

There were significant reductions in the mean scores at the end of 3 months for patients taking Astaxanthin oleoresin complex but not for the Placebo group. There were no significant differences between Astaxanthin oleoresin complex and Placebo group at Basal values. There were significant differences between Astaxanthin oleoresin complex and Placebo groups at 3 months.

Laquesne's Index—

Laquesne's index is the Functional index for Osteoarthritis of the knee. Assessment is carried out on a) Pain/discomfort—during nocturnal bed rest, morning stiffness or regressive pain after rising, after standing for 30 minutes; and b) Physical functions—maximum distance walked, activities of daily living like able to climb up a standard flight of stairs, able to climb down a standard flight of stairs, able to squat or bend on the knees, able to walk on uneven ground. The Laquesne's index results are given in Table 6.

There were significant reductions in mean scores for the patients taking Astaxanthin oleoresin complex at the end of 3 months but not for the Placebo group. There were no significant differences between astaxanthin oleoresin complex and Placebo groups at Basal values. There were significant differences between astaxanthin oleoresin complex and Placebo groups at 3 months.

Sleep Scale—

Sleep is an important element of functioning and well being. Sleep Scale was originally developed in the Medical Outcomes Study (MOS) intended to assess the extent of sleep problems. The Medical Outcomes Study Sleep Scale includes 12 items assessing sleep disturbance, sleep adequacy, somnolence, quantity of sleep, snoring, and awakening short of breath or with a headache. A sleep problems index, grouping items from each of the former domains, is also available. This assessment evaluated the psychometric properties of MOS-Sleep Scale in Osteoarthritis patients taking Astaxanthin oleoresin complex and Placebo group. The results on Sleep scale MOS is given in Table 7.

There were significant reductions in the mean scores for patients taking astaxanthin oleoresin complex at the end of 3 months but not for the Placebo group. There were no significant differences between astaxanthin oleoresin complex group and Placebo group at Basal values. There were significant differences between astaxanthin oleoresin complex group and Placebo group for most of the variables.

MMP3 (Matrix Metalloproteinase 3) Assay—

Assessment of Osteoarthritis symptoms based on haematological studies, specifically MMP3 (Matrix metalloproteinase 3) were carried out in clinical parameters since Osteoarthritis patients show elevated levels of MMP3 in blood as well as in synovial fluid. The elevated levels cause significant tissue damage through cartilage destruction. The results of the MMP3 analysis on Osteoarthritis patients before and after 3 months of administering with astaxanthin oleoresin complex are given in FIG. 2. The results of the MMP3 analysis on Osteoarthritis patients before and after 3 months of administering with Placebo are given in FIG. 3. MMP3 levels did not show significant change but the trend is towards reduction.

In all, 70 subjects were recruited for the study in a randomized manner. The patients were explained the nature of the study as well as active (astaxanthin oleoresin complex softgels containing 15 mg astaxanthin) and placebo treatments. An informed written consent was obtained from the subjects prior to the commencement of the study. At the commencement of the study patient subjects were clinically examined and blood samples were collected for CBC/ESR & MMP3 study. Specific orthopaedic and radiological examinations were performed. The patient subjects were assigned placebo and active treatment in a random manner for a period of 12 weeks. Patient subjects were advised to continue with their other routine treatments, if any. At the end of 4 weeks the subjects were called for a second visit in order to refill the samples. The same procedure was carried out in third visit and the procedure of the first visit was repeated in fourth visit. Results were tabulated by data entry operators and detailed statistical analysis was performed using those results. At the base level the groups were similar and comparable.

Advantages of the Invention

Total Health Assessment score (Arising, Dressing, Eating, Walking, Hygiene, Grip, Reaching, Daily activities) exhibited significant changes between Astaxanthin oleoresin complex and Placebo group (P<0.001). Improvement was seen in all the parameters of daily activities.

WOMAC INDEX exhibited significant differences (P<0.001). This score is unique for the functional abilities in patients with chronic joint disorders such as Osteoarthritis.

VAS Pain parameters (Pain+Physical) score: There were significant reductions in the mean scores at the end of treatment for patients taking astaxanthin oleoresin complex but not for Placebo P (<0.001). It is suggestive of improvement in the pain related aspects of Osteoarthritis.

Laquesne's index: (Functional Index for OA of knee): There were significant reductions in the mean scores at the end of treatment for patients taking Astaxanthin oleoresin complex but not for Placebo (P<0.05).

Sleep scale from the medical outcomes study: There were significant reductions in the mean scores at the end of treatment for patients taking astaxanthin oleoresin complex but not for Placebo (P<0.001).

There was significant difference between the average sleep each night (hrs). Patients taking astaxanthin oleoresin complex had higher sleep than Placebo group (P<0.01).

Improvement in the sleep time clearly indicates efficacy of the treatment with astaxanthin oleoresin complex. Astaxanthin helps to get better sleep as is evident from sleep score. This is due to reduction in pain and other symptoms of the disorder MMP3 did not show significant change but the trend is towards reduction. Reduction in MMP3 levels are suggestive of improving cartilage health due to reduction in the process of cartilage destruction in a positive manner although there is neither direct proof to this effect nor statistically significant effect in the present study. No change in the radiological picture was seen. No noteworthy side effect/intolerance was noted during the study period. Astaxanthin oleoresin complex appears to be safe for general consumption.

Astaxanthin oleoresin complex extracted through polar solvents from *Haematococcus pluvialis* alga may be suitable for the patients in the early stage of the Osteoarthritis to prevent the progression of the disorder. It may be useful to the patients with established Osteoarthritis to provide symptomatic relief from pain and improved quality of life. Astaxanthin oleoresin complex improves symptoms like pain as well as quality of physical activities of daily life in a significant manner. Osteoarthritis is seen to mark its presence at a younger age in India. It would be appropriate to initiate the treatment with Astaxanthin oleoresin complex right from the beginning as soon as the diagnosis is arrived at. Study with larger sample size at different centres is recommended to study the mechanism of action of Astaxanthin oleoresin complex in Osteoarthritis further.

TABLE 1

Carotenoid Profile of *Haematococcus Pluvialis* Cell Powder and Astaxanthin Oleoresin Complex

| Carotenoids | Cell powder | Astaxanthin Oleoresin complex 5% |
| --- | --- | --- |
| Beta-carotene | 0.62 ± 0.01 | 0.62 ± 0.01 |
| Canthaxanthin | 1.21 ± 0.03 | 1.20 ± 0.03 |
| Astacene | 3.09 ± 0.06 | 3.09 ± 0.06 |
| Semiastacene | 1.35 ± 0.03 | 1.35 ± 0.03 |
| Dicis astaxanthin | 1.07 ± 0.02 | 1.03 ± 0.05 |
| Trans astaxanthin | 75.70 ± 1.53 | 75.75 ± 1.51 |

TABLE 1-continued

Carotenoid Profile of *Haematococcus Pluvialis* Cell Powder and Astaxanthin Oleoresin Complex

| Carotenoids | Cell powder | Astaxanthin Oleoresin complex 5% |
|---|---|---|
| 9 cis astaxanthin | 9.20 ± 0.77 | 9.19 ± 0.77 |
| 13 cis astaxanthin | 6.10 ± 0.94 | 6.08 ± 0.93 |
| Lutein | 1.66 ± 0.03 | 1.65 ± 0.03 |

TABLE 2

Proximate Analysis, Carotenoid Profile and Fatty Acid Profile of Astaxanthin Oleoresin Complex

| PARAMETER | Astaxanthin oleoresin complex 5% |
|---|---|
| PHYSICAL | |
| Appearance | Free flow |
| Color | Dark red |
| PROXIMATE | |
| Protein % | 0.95 ± 0.03 |
| Carbohydrate % | 0.11 ± 0.01 |
| Lipid % | 94.89 ± 0.12 |
| Ash % | 3.82 ± 0.08 |
| Moisture % | 0.23 ± 0.02 |
| Carotenoids | 5.14 ± 0.04 |
| CAROTENOIDS % | |
| Total carotenoids | 5 |
| Total astaxanthin | 4.68 |
| [all-trans-astaxanthin | [3.90 |
| 9-cis-astaxanthin | 0.47 |
| 13-cis-astaxanthin | 0.31 |
| 15-cis-astaxanthin | 0 |
| Dicis-astaxanthin] | 0.05] |
| Betacarotene | 0.03 |
| Canthaxanthin | 0.06 |
| Lutein | 0.08 |
| FATTY ACID PROFILE, Area % | |
| C14:0 Myristic acid | 0.23 |
| C 15:0 Pentadecanoic acid | 0.1 |
| C 16:0 Palmitic acid | 24.57 |
| C16:1 Palmitoleic acid | 0.57 |
| C 16:2 Hexadeca dienoic acid | 0.45 |
| C 16:3 Hexadecatrienoic acid | 0.14 |
| C 16:4 Hexadecatetraenoic acid | 1.15 |
| C17:0 Heptadecanoic acid | 2.14 |
| C 18:0 Stearic acid | 1.61 |
| C18:1 Oleic acid | 38.93 |
| C 18:2 Linoleic acid | 17.22 |
| C 18:3, n-6 Gamma linolenic acid | 0.84 |
| C 18:3, n-3 Alpha linolenic acid | 8.14 |
| C 18:4 Octadeca tetraenoic acid | 1.3 |

TABLE 2-continued

Proximate Analysis, Carotenoid Profile and Fatty Acid Profile of Astaxanthin Oleoresin Complex

| PARAMETER | Astaxanthin oleoresin complex 5% |
|---|---|
| C20:2 Eicosadienoic acid | 0.81 |
| C20:4 Arachidonic acid | 0.85 |
| C22:0 Behenic acid | 0.5 |

TABLE 3

Total Health Assessment Score

| | Duration | | | | |
|---|---|---|---|---|---|
| Treatments | Basal | 1 month | 2 months | 3 months | Significance level |
| Astaxanthin | 18 | 14.68 | 13.19 | 12.13 | S, $P < 0.001$ |
| Placebo | 20.25 | 19.8 | 19.48 | 19.51 | NS, $P = 0.4$ |

S = Significant,
NS = Not Significant,
P = Probability

TABLE 4

WOMAC Score

| | Duration | | | | Significance |
|---|---|---|---|---|---|
| Treatments | Basal | 1 month | 2 months | 3 months | level |
| Astaxanthin | 36.39 | 31.87 | 28.42 | 26.52 | S, $P < 0.001$ |
| Placebo | 38.07 | 36.62 | 36.59 | 36.1 | NS, $P = 0.6$ |

S = Significant,
NS = Not Significant,
P = Probability

TABLE 5

VAS Pain Parameters Score

| | Duration | | | | Significance |
|---|---|---|---|---|---|
| Treatments | Basal | 1 month | 2 months | 3 months | level |
| Astaxanthin | 891.94 | 828.71 | 772.58 | 748.39 | S, $P < 0.001$ |
| Placebo | 945.86 | 923.28 | 916.21 | 915.17 | NS, $P = 0.1$ |

S = Significant,
NS = Not Significant,
P = Probability

TABLE 6

Laquesne's Index

| Parameters | | Astaxanthin | Placebo | Significance level |
|---|---|---|---|---|
| 1. During nocturnal bed rest | Basal | 0.6 +/− 0.7 | 0.6 +/− 0.7 | NS, $P = 1.0$ |
| | 3 months | 0.8 +/− 0.7 | 0.5 +/− 0.7 | S, $P = 0.05$ |
| 2. Morning stiffness or regressive pain after rising | Basal | 0.9 +/− 0.6 | 0.6 +/− 0.7 | NS, $P = 0.9$ |
| | 3 months | 0.6 +/− 0.6 | 0.6 +/− 0.5 | NS, $P = 0.9$ |
| 3. After standing for 30 minutes | Basal | 0.4 +/− 0.5 | 0.6 +/− 0.7 | NS, $P = 0.9$ |
| | 3 months | 0.3 +/− 0.6 | 0.5 +/− 0.7 | S, $P = 0.05$ |
| 4. Maximum distance walked | Basal | 1.3 +/− 0.7 | 1.7 +/− 1.3 | NS, $P = 0.9$ |
| | 3 months | 0.6 +/− 0.5 | 1.7 +/− 1.3 | S, $P = 0.001$ |

TABLE 6-continued

Laquesne's Index

| Parameters | | Astaxanthin | Placebo | Significance level |
|---|---|---|---|---|
| 5. Activities of daily living | | | | |
| a) Able to climb up a standard flight of stairs | Basal | 0.8 +/− 0.5 | 0.9 +/− 0.3 | NS, P = 0.9 |
| | 3 months | 0.7 +/− 0.5 | 1.0 +/− 0.4 | S, P = 0.03 |
| b) Able to climb down a standard flight of stairs | Basal | 1.3 +/− 0.3 | 1.6 +/− 0.9 | NS, P = 0.9 |
| | 3 months | 0.9 +/− 0.6 | 1.6 +/− 0.9 | S, P = 0.03 |
| c) Able to squat or bend the knees | Basal | 1.3 +/− 0.3 | 1.6 +/− 0.9 | NS, P = 0.9 |
| | 3 months | 0.9 +/− 0.6 | 1.6 +/− 0.9 | S, P = 0.03 |
| d) Able to walk on uneven ground | Basal | 1.3 +/− 0.3 | 1.6 +/− 0.9 | NS, P = 0.9 |
| | 3 months | 0.9 +/− 0.6 | 1.6 +/− 0.9 | S, P = 0.03 |

S = Significant,
NS = Not Significant,
P = Probability

TABLE 7

Sleep Scale MOS

| Sleep parameters | | Astaxanthin | Placebo | Significance level |
|---|---|---|---|---|
| 1. Time to fall asleep (min) during the past 4 weeks | Basal | 2.3 +/− 1.3 | 2.6 +/− 1.3 | NS, P = 0.9 |
| | 3 months | 1.6 +/− 1.1 | 2.5 +/− 1.3 | S, P < 0.001 |
| 2. Average sleep each night (hours during last 4 weeks) | | 6. +/− 1.3 | 5. +/− 1.8 | S, P < 0.001 |
| 3. Feel your sleep was not quiet? | Basal | 3. +/− 1.9 | 3. +/− 1.9 | NS, P = 0.9 |
| | 3 months | 2.6 +/− 2.1 | 3.8 +/− 2.1 | S, P = 0.02 |
| 4. Get enough sleep to feel rested upon? | Basal | 3.8 +/− 1.9 | 3.8 +/− 1.9 | NS, P = 1.0. |
| | 3 months | 2.9 +/− 2.1 | 3.6 +/− 2.1 | S, P = 0.03 |
| 5. Awaken short of breath or with headache? | Basal | 5.6 +/− 1.2 | 4.6 +/− 2.2 | NS, P = 0.6 |
| | 3 months | 5.6 +/− 1.2 | 4.5 +/− 2.8 | NS, P = 0.6 |
| 6. Feel drowsy or sleepy during day? | Basal | 5. +/− 1.2 | 4. +/− 2.2 | NS, P = 0.6 |
| | 3 months | 5.7 +/− 1.8 | 4.5 +/− 2.8 | NS, P = 0.6 |
| 7. Have trouble falling asleep? | Basal | 3.6 +/− 2.7 | 4.6 +/− 2.2 | NS, P = 0.3 |
| | 3 months | 4.4 +/− 2.1 | 4.5 +/− 2.8 | NS, P = 0.9 |
| 8. Awaken during your sleep time and have trouble in falling sleep again? | Basal | 4.1 +/− 2.9 | 4.6 +/− 2.2 | NS, P = 0.7 |
| | 3 months | 4.9 +/− 2.3 | 4.5 +/− 2.8 | NS, P = 0.7 |
| 9. Have trouble staying awake during the day? | Basal | 4.7 +/− 1.8 | 4.6 +/− 2.2 | NS, P = 0.9 |
| | 3 months | 5.4 +/− 1.8 | 4.5 +/− 2.8 | S, P = 0.05 |
| 10. Snore during your sleep? | Basal | 5.5 +/− 1.1 | 4.4 +/− 1.5 | NS, P = 0.2 |
| | 3 months | 5.7 +/− 0.8 | 4.8 +/− 1.3 | S, P = 0.05 |
| 11. Take naps (5 min. or longer) during the day? | Basal | 4.1 +/− 1.5 | 4.4 +/− 1.5 | NS, P = 0.6 |
| | 3 months | 3.7 +/− 1.5 | 4.8 +/− 1.3 | S, P = 0.05 |
| 12. Get the amount of sleep you needed? | Basal | 3.2 +/− 1.8 | 4.5 +/− 1.5 | NS, P = 0.6 |
| | 3 months | 3.7 +/− 1.8 | 4.8 +/− 1.3 | S, P = 0.05 |

S = Significant,
NS = Not Significant,
P = Probability

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for treating and alleviating symptoms of joint pain comprising orally administering to a person having joint pain a therapeutic amount of a dietary supplement composition, comprising 0.5 to 12.0 mg of astaxanthin derived from *Haematococcus pluvialis*, 10 to 70 mg of pro-inflammatory low molecular weight microbial fermented sodium hyaluronate fragments free from amino acid conjugation and having a molecular weight of 0.5 to 300 kilodaltons (kDa), and 50 to 500 mg of krill or algae oil or phospholipid, and wherein the astaxanthin is 0.1 to 15 percent by weight of the krill or algae oil or phospholipid, and the dietary supplement composition is in the form of a single dosage capsule.

2. The method according to claim 1, wherein the dietary supplement composition further includes a pharmaceutical or food grade diluent.

3. The method according to claim 1, wherein the phospholipid is selected from the group consisting of Phosphatidylcholine, Phosphatidylethanolamine, Phosphatidylserine, Phosphatidylinositol, Phosphatidic acid, Lyso-Phosphatidylcholine, Lyso-Phosphatidylethanolamine, and Lyso-Phosphatidylserine.

4. The method according to claim 1, wherein the phospholipid comprises at least one of a plant, algae and animal source.

5. The method according to claim 1, further comprising forming the dietary supplement composition by dispersing the astaxanthin derived from *Haematococcus pluvialis* under high shear conditions into the krill or algae oil or phospholipid.

* * * * *